(12) United States Patent
Petraglio et al.

(10) Patent No.: US 10,675,154 B2
(45) Date of Patent: Jun. 9, 2020

(54) OSTEOCHONDRAL LOCAL PROSTHETIC INSERT

(71) Applicant: BONE AND JOINT SOLUTIONS SA, Lugano (CH)

(72) Inventors: Matteo Petraglio, San Pietro (CH); Ettore Taverna, Cabbio (CH)

(73) Assignee: BONE AND JOINT SOLUTIONS SA, Lugano (CH)

( * ) Notice: Subject to any disclaimer, the term of this patent is extended or adjusted under 35 U.S.C. 154(b) by 110 days.

(21) Appl. No.: 15/953,976

(22) Filed: Apr. 16, 2018

(65) Prior Publication Data
US 2018/0296355 A1    Oct. 18, 2018

(30) Foreign Application Priority Data

Apr. 14, 2017    (IT) ........................ 102017000042055

(51) Int. Cl.
*A61F 2/40* (2006.01)
*A61F 2/30* (2006.01)
(Continued)

(52) U.S. Cl.
CPC ........ *A61F 2/4003* (2013.01); *A61B 17/1684* (2013.01); *A61B 17/8605* (2013.01);
(Continued)

(58) Field of Classification Search
CPC ................. A61F 2/4618; A61F 2/4014; A61F 2002/30759; A61F 2002/4007;
(Continued)

(56) References Cited

U.S. PATENT DOCUMENTS

| 5,885,297 A | 3/1999 | Matsen, III |
| 6,520,964 B2 | 2/2003 | Tallarida et al. |

(Continued)

FOREIGN PATENT DOCUMENTS

| DE | 102005014624 A1 * | 10/2006 | ......... A61B 17/1635 |
| EP | 1867303 A1 | 12/2007 | |

(Continued)

OTHER PUBLICATIONS

Translation of DE102005014624A1 retrieved from espacenet on Sep. 28, 2019 (Year: 2019).*

(Continued)

*Primary Examiner* — Megan Y Wolf
(74) *Attorney, Agent, or Firm* — Underwood & Associates, LLC

(57) ABSTRACT

The present invention refers to an osteochondral local prosthetic insert for partial humeral joint reconstitution by reconstitution of the bone anatomical sphericity to treat bone lesions, in particular Hill-Sachs lesions. The local osteochondral prosthetic insert is a rigid monolithic body having a truncated-cone shape, the proximal diameter greater than the distal diameter, the proximal end of convex shape and rounded at the corners, and a tapered distal end. The lateral surface of the insert shows in the middle-distal part a non-return shaping that allows the maintenance of the position defined in the surgical operation. The proximal end is convex in order to better adapt to the local bone sphericity and has recesses for the manipulation and positioning through dedicated tools.

13 Claims, 18 Drawing Sheets

(51) Int. Cl.
*A61F 2/46* (2006.01)
*A61B 17/86* (2006.01)
*A61B 17/16* (2006.01)
*A61B 17/04* (2006.01)
*A61B 17/92* (2006.01)

(52) U.S. Cl.
CPC ...... *A61F 2/30756* (2013.01); *A61F 2/30771* (2013.01); *A61F 2/4014* (2013.01); *A61F 2/4618* (2013.01); *A61B 17/0401* (2013.01); *A61B 17/86* (2013.01); *A61B 2017/922* (2013.01); *A61F 2002/3085* (2013.01); *A61F 2002/30112* (2013.01); *A61F 2002/30224* (2013.01); *A61F 2002/30299* (2013.01); *A61F 2002/30616* (2013.01); *A61F 2002/30795* (2013.01); *A61F 2002/30822* (2013.01); *A61F 2002/30878* (2013.01); *A61F 2002/30881* (2013.01); *A61F 2002/30886* (2013.01); *A61F 2002/4007* (2013.01); *A61F 2002/4677* (2013.01); *A61F 2002/4681* (2013.01); *A61F 2310/00011* (2013.01); *A61F 2310/00023* (2013.01)

(58) Field of Classification Search
CPC .......... A61F 2002/4677; A61F 2/30756; A61F 2/4003; A61F 2/4612; A61B 17/1684; A61B 2017/922

See application file for complete search history.

(56) References Cited

U.S. PATENT DOCUMENTS

| | | |
|---|---|---|
| 7,678,151 B2 | 3/2010 | Ek |
| 8,690,958 B2 | 4/2014 | Klawitter et al. |
| 8,777,956 B2 | 7/2014 | Hoeppner et al. |
| 9,364,333 B1 | 6/2016 | Paulos |
| 2004/0225367 A1 | 11/2004 | Glien et al. |
| 2005/0065612 A1 | 3/2005 | Winslow |
| 2006/0009852 A1 | 1/2006 | Winslow et al. |
| 2006/0036328 A1 | 2/2006 | Parrott et al. |
| 2006/0241779 A1 | 10/2006 | Lakin |
| 2007/0093896 A1* | 4/2007 | Malinin ............ A61B 17/1604 623/14.12 |
| 2008/0021564 A1 | 1/2008 | Gunther |
| 2008/0234829 A1 | 9/2008 | Mutchler |
| 2008/0249632 A1 | 10/2008 | Stone |
| 2010/0049322 A1 | 2/2010 | Mckay |
| 2010/0191340 A1 | 7/2010 | Dryfuss |
| 2010/0256758 A1 | 10/2010 | Gordon et al. |
| 2011/0009964 A1 | 1/2011 | Schwartz et al. |
| 2011/0054624 A1 | 3/2011 | Iannotti |
| 2011/0257753 A1 | 10/2011 | Gordon et al. |
| 2011/0313533 A1 | 12/2011 | Gunther |
| 2013/0190882 A1 | 7/2013 | Humphrey |
| 2016/0143749 A1* | 5/2016 | Holovacs ............ A61F 2/4081 623/19.11 |
| 2017/0360566 A1* | 12/2017 | Sikora ................ A61F 2/30734 |

FOREIGN PATENT DOCUMENTS

| | | |
|---|---|---|
| EP | 1278460 B1 | 4/2009 |
| FR | 2926212 A1 | 7/2009 |
| WO | 2004075777 A2 | 9/2004 |
| WO | 2011081797 A1 | 7/2011 |
| WO | 2015/112307 A1 | 7/2015 |

OTHER PUBLICATIONS

Ministero dello Sviluppo Economico; Early Search Report for Italian Patent Application No. 102017000042055; dated Dec. 21, 2017; Munich. Submitted herewith as IDS-REF_Early-Search-Report.pdf.

Bark, S.; Renken, F.; Schulz, A.P.; Paech, A.; Gille, J., Arthroscopic-Assisted Treatment of a Reversed Hill-Sachs Lesion: Description of a New Technique Using Cerament; Case Reports in Orthopedics, V 2015, Article ID 789203; Hindawi Publishing Corporation; Received Oct. 29, 2014.

Black, Loren O., Ko, Kevin Jai-Wei, Quilici, Samantha M., Crawford, Dennis C.; Fresh Osteochondral Allograft to the Humeral head for Treatment of an Engaging Reverse Hill-Sachs Lesion; The Orthopaedic Journal of Sports Medicine, 4(11), 2325967116670376, 2016.

* cited by examiner

FIG.12
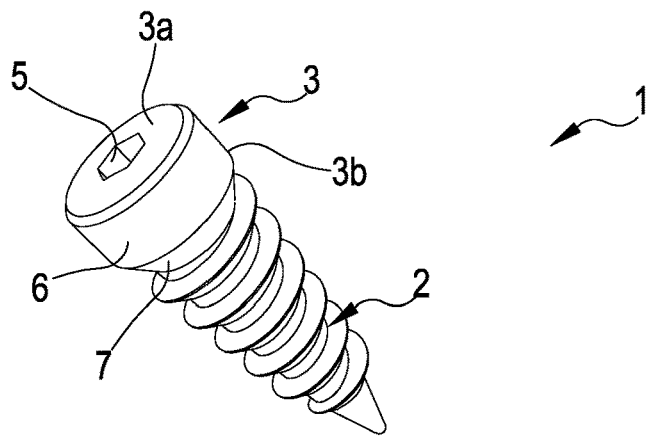
FIG.13
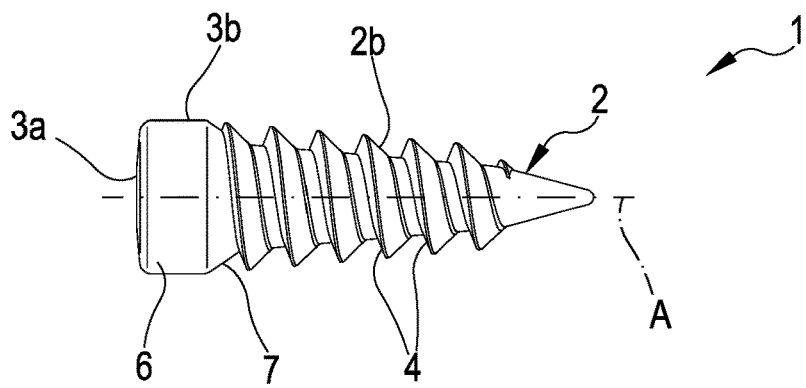
FIG.14
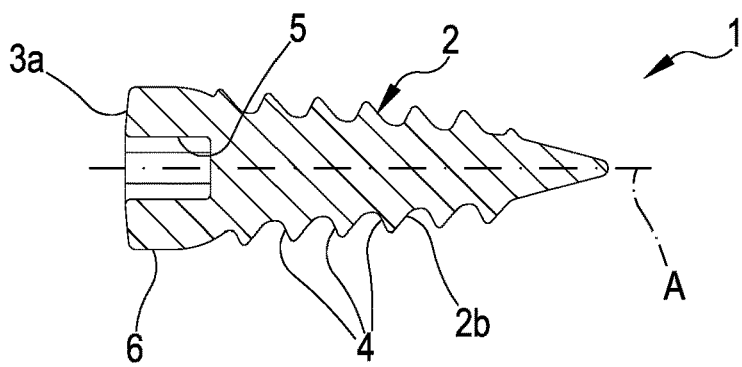
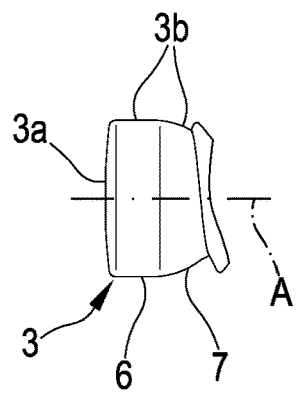
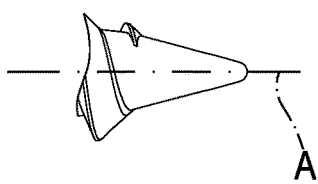
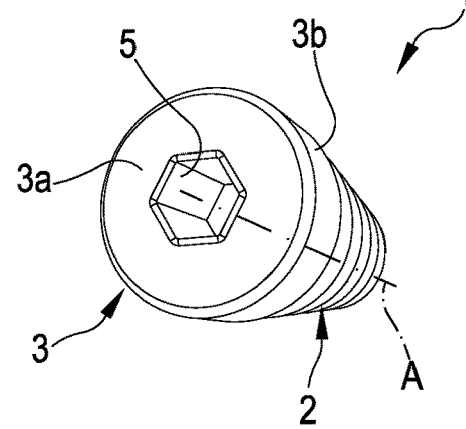
FIG.15　　　FIG.16　　　FIG.17

FIG.18
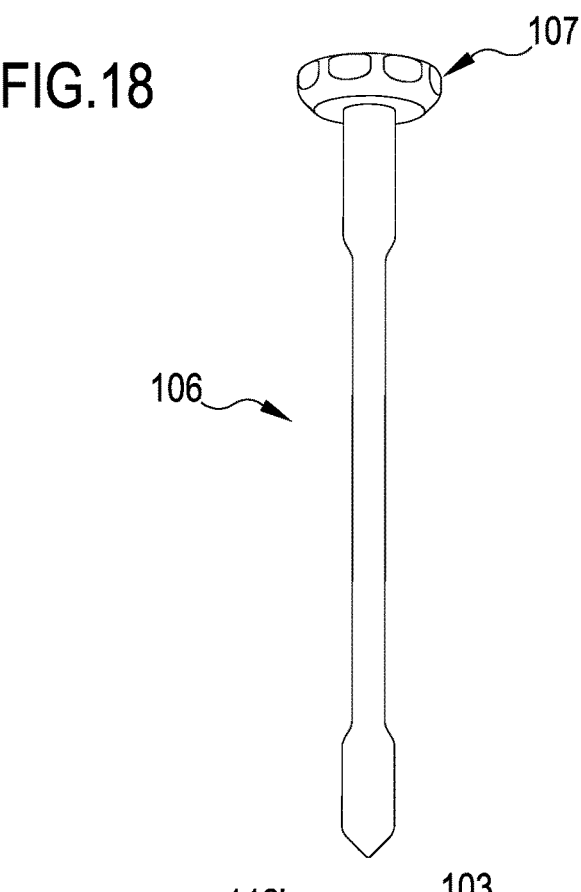
FIG.19
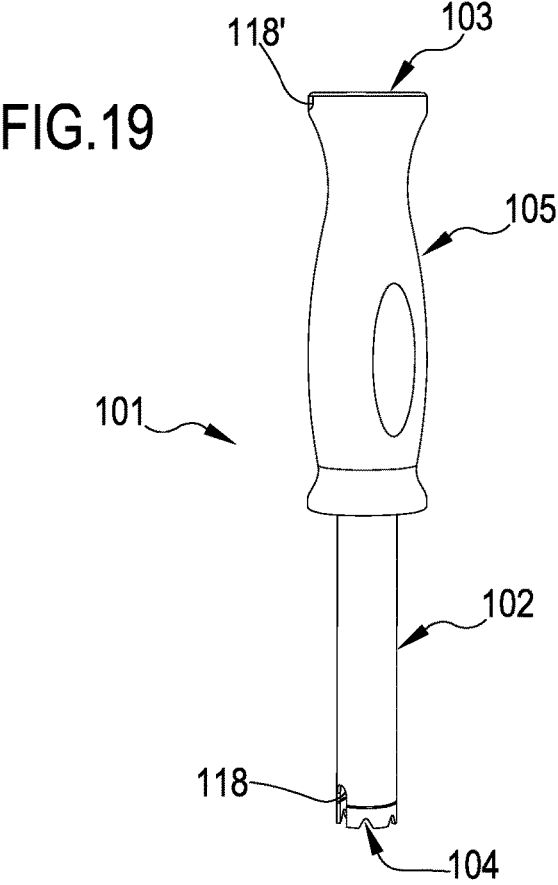
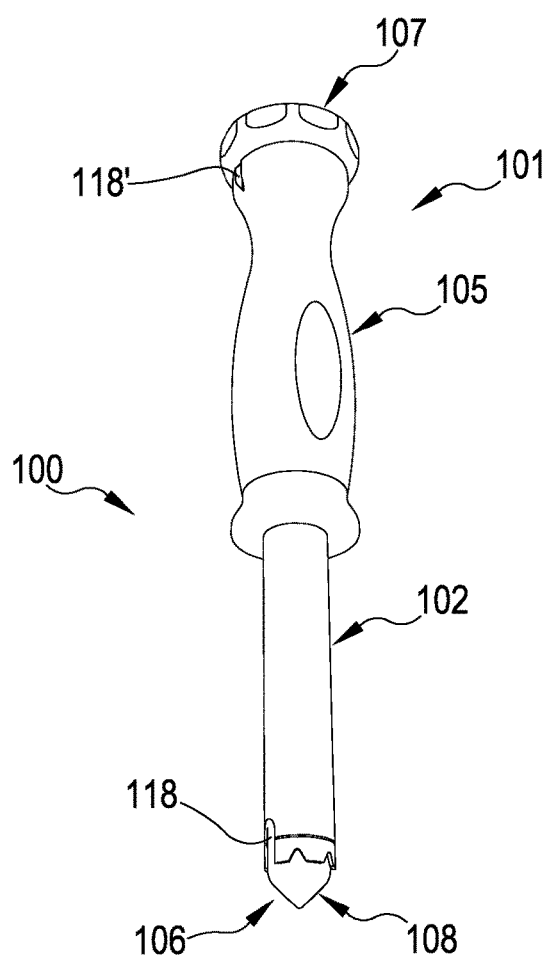
FIG.20

FIG.21
FIG.22
FIG.23
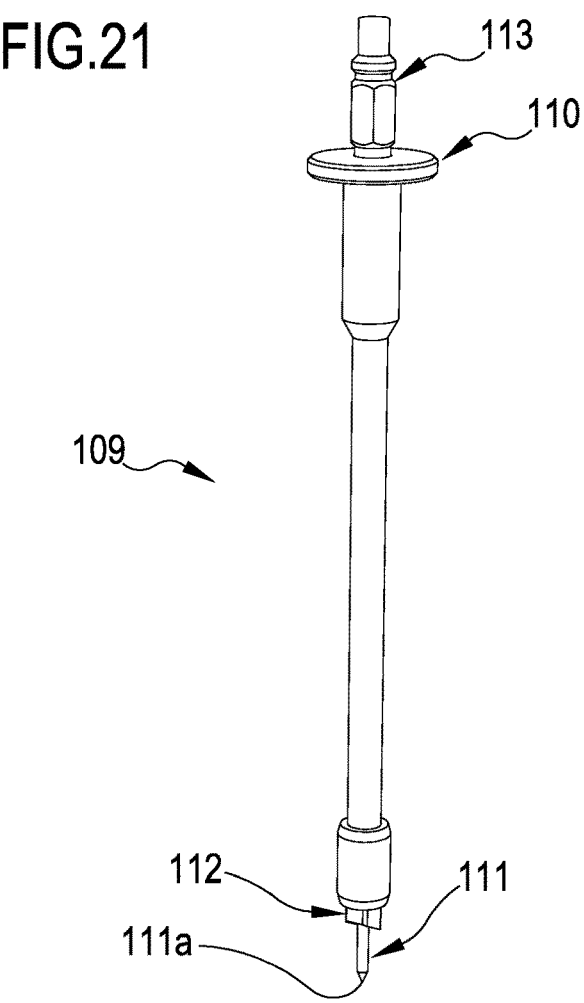
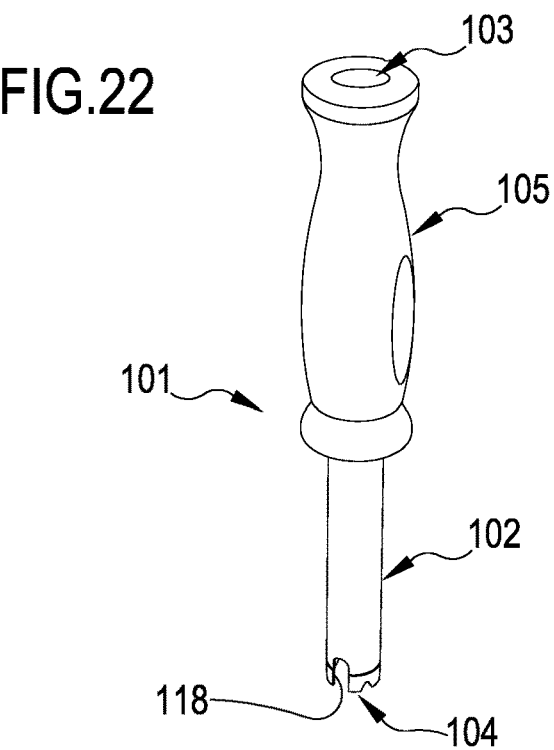
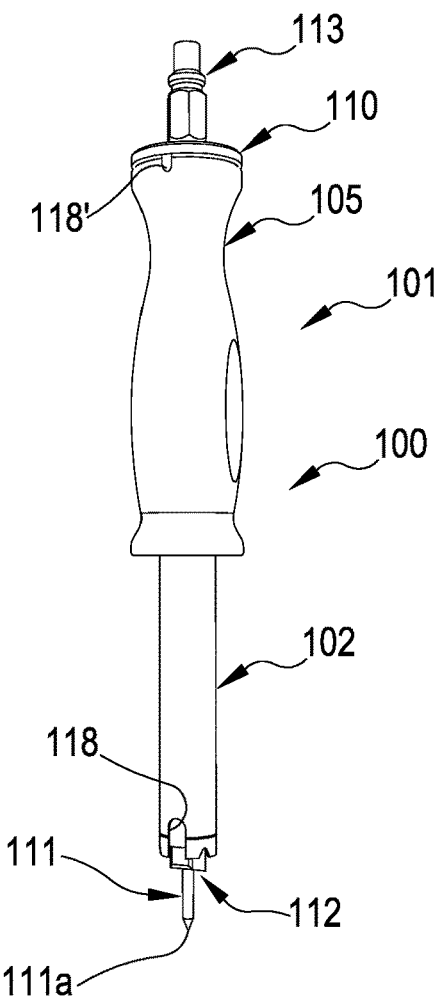

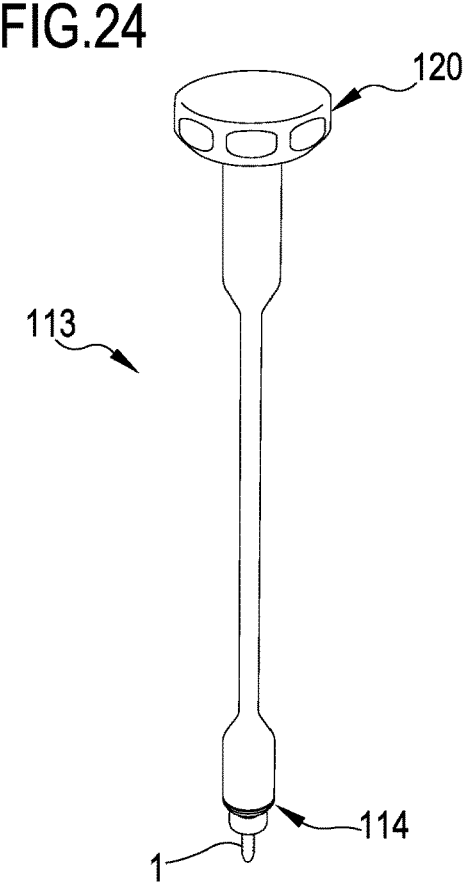
FIG.24
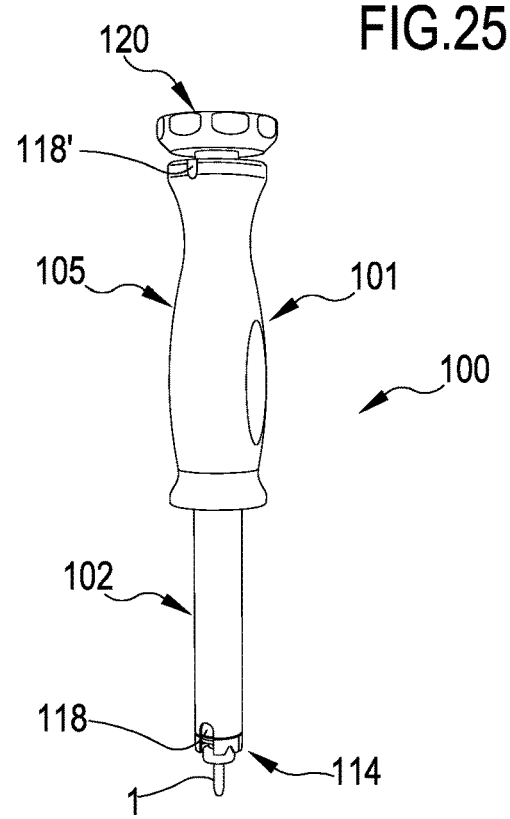
FIG.25
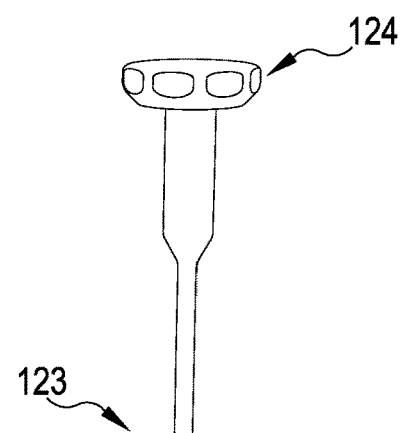
FIG.26
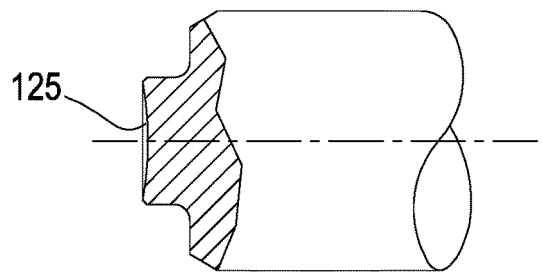
FIG.24A
FIG.26A FIG.27
FIG.28
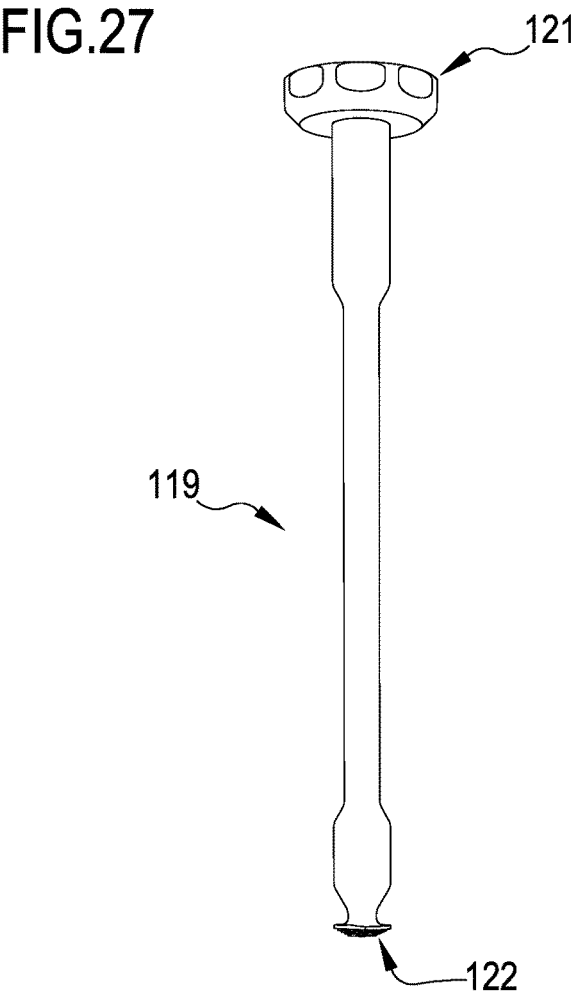
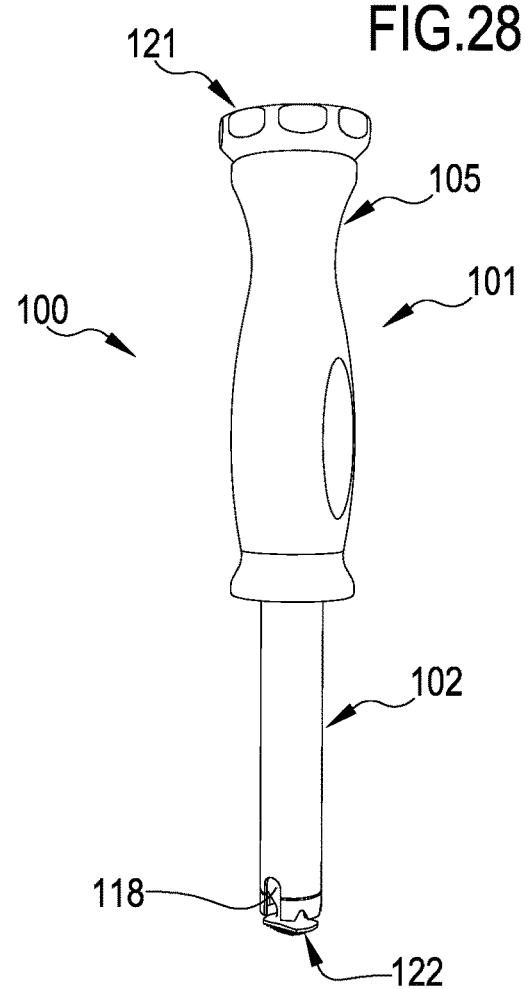
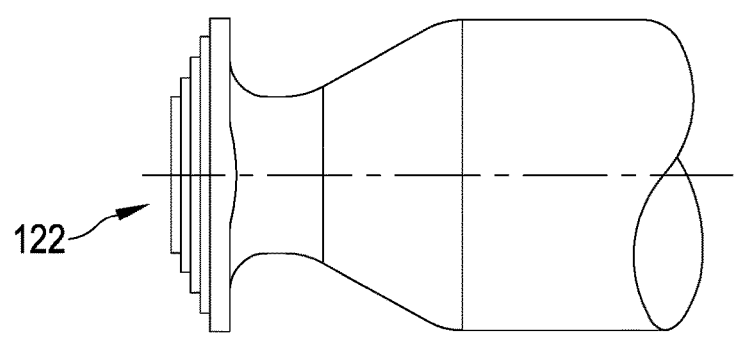
FIG.27A FIG.36
FIG.37
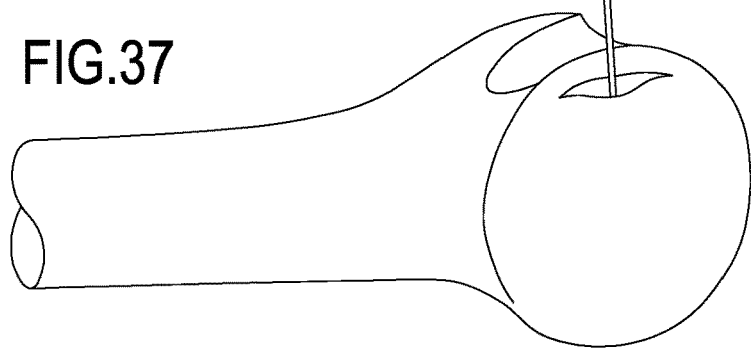
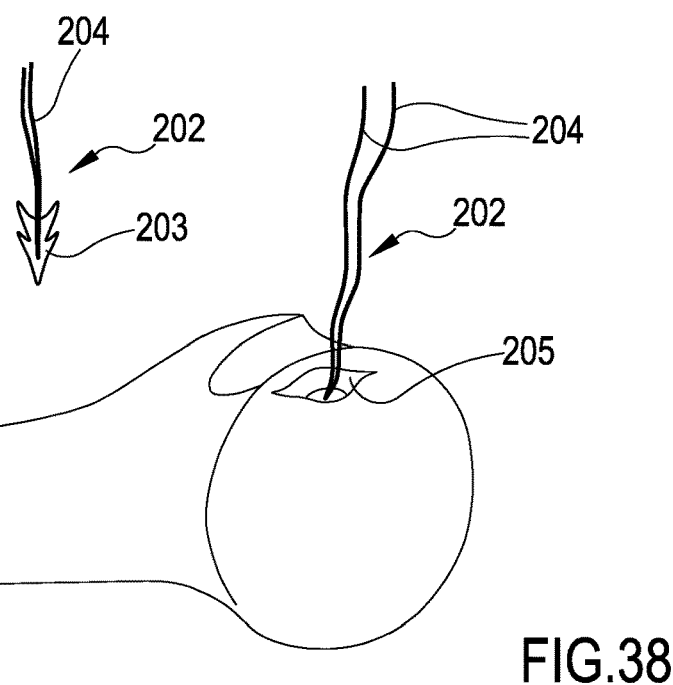
FIG.38

OSTEOCHONDRAL LOCAL PROSTHETIC INSERT

FIELD OF THE INVENTION

The present invention relates to an osteochondral local prosthetic insert for partial humeral joint reconstitution by reconstituting of the humeral bone anatomical sphericity. More specifically, the present invention relates to a prosthetic insert for the local reconstitution of lesions and/or osteochondral depressions in the humerus by open or arthroscopic surgery. The invention also relates to a use of such insert for partial humeral bone reconstitution and in particular for treating the Hill-Sachs lesion with partial humeral bone head reconstitution. The invention also relates to a medical kit for partial humeral joint reconstitution, in particular for treating the Hill-Sachs lesion. The invention also relates to a method for shoulder joint reconstitution.

STATE OF THE ART

The shoulder joint allows a greater number of movements with respect to any other joint in the human body, thus being particularly susceptible to dislocation and traumatic subluxation, among which the anterior-inferior dislocation is the most frequent. In such case, the humerus is detached from the glenoid component, realizing a gleno-humeral dislocation. The front traumatic dislocation (the most frequent) occurs when the humerus is displaced in forward and downward direction with respect to the glenoid. In 50% of cases a new dislocation occurs later on. In relapsing dislocations a traumatism may not be present. Those who are most at risk for such problems are the young males who practice sports and activities involving contacts and collisions. In case of multiple dislocations, anatomo-pathological lesions tend to worsen, affecting both soft tissues and the bone of the humeral glenoid, causing apprehension and progressive disability that can be treated by surgery. In a high percentage of cases, the gleno-humeral anterior-inferior dislocation causes a forced compression of the humeral head against the front edge of the glenoid generating in such case a posterior-lateral cortical depression in the humeral head, called Hill-Sachs injury or fracture (hereinafter Hill-Sachs lesion). In association with the Hill-Sachs lesion, also lesions of soft or bone tissues in various associations may be present, such as: Bankhart lesion, ALPSA lesion, erosion or bony Bankhart. All these lesions contribute to reducing the stability of the gleno-humeral increasing the chances of relapsing dislocations. The joint stabilization occurs through anatomical and non-anatomical interventions by acting on both articular heads (glenoid and humeral head) and on the soft tissues that connect them (Labrum, capsula, ligaments, etc.). The majority of surgical stabilization operations are techniques for repairing the soft tissues at the glenoid (reinsertion of the labrum and of the ligaments, repair of Bankhart injury, repair of ALPSA lesion, etc.). Even the bone stabilization interventions are directed at the glenoid component (intervention of Latarjet, Bristow, Bone Block, etc.) while the surgical procedures performed on the humeral head are at the moment less frequent (HAGL and RHAGL repair and Hill-Sachs lesion remplissage). To date, there are no standardized bone-type interventions for the stabilization of the Hill-Sachs lesion. The reconstitution of the sphericity of the anatomic humeral head, i.e. the treatment of Hill-Sachs lesion is a viable way to stabilize the joint. Recent studies have shown that the simultaneous presence of a bone defect of the humeral head (Hill-Sachs lesion) in combination with an erosion of the glenoid rim (bony erosion Bankhart) greatly reduces the joint stability. The reconstitution operations for the bony stock of the glenoid are numerous and standardized, while to date there are no described interventions for bone reconstitution of the humeral head. Excluding the partial or total arthroplasty of the shoulder and the reconstitution technique, today the technique called day "Remplissage" or "Fill-in" is the only filling/topping up/saturation surgery intervention available for the Hill-Sachs lesion. It is an infraspinatus tenodesis, which consists in the use of the articular capsule of the tendon and sometimes of the infraspinatus muscle, fixed by means of one or more anchor sutures within the lesion, as filler means to prevent the engagement (meshing) of the humeral head on the glenoid. The remplissage technique is quite always associated with another stabilization technique at the level of the anterior glenoid rim. The known remplissage techniques involve various drawbacks, and in particular they do not reconstitute the sphericity of the anatomic humeral head, but only fill the cavity with soft tissues. Furthermore, the known remplissage techniques generate an extra load on the rotator cuff. Furthermore, the known remplissage techniques involve a possible reduction of the joint mobility. An aim of the present invention is to provide an osteochondral local prosthetic insert, a use of such insert, a method for partial humeral head reconstitution and a medical kit for partial humeral joint reconstitution, allowing to overcome the drawbacks of the cited prior art solutions and aforementioned techniques. Another aim of the invention is to provide a prosthetic insert, a medical kit, a use of a prosthetic insert and a method for treating the Hill-Sachs lesion allowing a local anatomical geometric reconstitution of a damaged articular surface. Another aim of the invention is to provide a prosthetic insert, a medical kit, a use of a prosthetic insert and a method for treating the Hill-Sachs lesion allowing the joint stabilization in patients who have a Hill-Sachs lesion by reconstituting the geometric anatomical bone sphericity of the humeral head. Another aim of the invention is to provide a prosthetic insert, a medical kit, a use of a prosthetic insert and a method for treating the Hill-Sachs lesion by restoring the stability of the humeral head without reducing the articular mobility and maintaining the patient's proprioception. Another aim of the invention is to provide a prosthetic insert, a medical kit, a use of a prosthetic insert and a method for treating the Hill-Sachs lesion without generating an additional load on the rotator cuff and/or joint capsule. Another aim of the invention is to provide a prosthetic insert, a medical kit, a use of a prosthetic insert and a method for treating the Hill-Sachs lesion minimizing the invasiveness of the surgical intervention. Auxiliary aims are the complete integration of the insert into the bone and the possibility to combine the use of the prosthetic insert with the "remplissage" technique. It is also provided a method minimizing invasiveness into the patient and making use of innovative instruments and surgical steps combined with well-known and spread surgical techniques and instruments, as apparent from the following description.

SUMMARY OF THE INVENTION

One or more of the cited aims is obtained by a prosthetic insert and/or a medical kit and/or a use of a prosthetic insert and/or a method for treating the Hill-Sachs lesion according to one or more of the attached claims. Further aspects of the invention, which can be combined with any of the attached claims and/or with any of the remaining cited aspects, are disclosed hereinafter.

According to a 1st independent aspect, a monolithic osteochondral local prosthetic insert (1) for partial humeral joint reconstitution is provided comprising a proximal load bearing head (3) defining an upper surface (3a) having a contour destined to substantially or at least partially match the recipient's humeral joint portion and a bottom surface (3c) opposite to the upper surface (3a), a main axis (A) extending from the upper surface (3a) to the bottom surface (3c), wherein the proximal load bearing head (3) is monolithic and has an overall dimension (s) in a plane orthogonal to the main axis (A) less than 25 mm, the proximal load bearing head (3) comprises:

- a lateral surface (3b) emerging from and extending transversal to the upper surface (3a), the lateral surface including a proximal portion (6) defining a surface parallel to the main axis (A) and a distal portion (7), extending from the proximal portion, defining a surface tapered in the direction of the main axis (A) moving towards bottom surface (3c), the distal portion being connected to the bottom surface (3c);
- a hollow (5) having an opening (5a) in correspondence of the upper surface (3a).

According to a further independent aspect, a monolithic osteochondral local prosthetic insert (1) for partial humeral joint reconstitution is provided comprising: a distal fixation body (2) extending along a main axis (A) and configured for engaging the humeral bone, said distal fixation body (2) comprising a shaped lateral surface (2b) defining a plurality of undercuts (4) to substantially prevent distal fixation body extraction from the bone; a proximal load bearing head (3) defining an upper surface (3a) having a contour destined to substantially or at least partially match the recipient's humeral joint portion, said proximal load bearing head (3) and said distal fixation body (2) being monolithic, wherein the proximal load bearing head (3) has an overall dimension (s) in a plane orthogonal to the main axis (A) less than 25 mm.

In a 2nd aspect in accordance with the 1st aspect, the insert (1) extends for at least 5 mm and is long less than 50 mm in the direction of the main axis (A), optionally long less than 14 mm in the direction of the main axis (A).

In a 3rd aspect in accordance with any of the previous aspects, the distal fixation body (2) has an overall dimension along the main axis (A) included between 5 mm and 40 mm.

In a 4th aspect in accordance with any of the previous aspects, the distal fixation body (2) extends for at least 15 mm and is long less than 30 mm in the direction of the main axis (A).

In a 5th aspect in accordance with any of the previous aspects, an overall length of the distal fixation body (2) in a direction orthogonal to the main axis (A) is comprised between 3 mm and 10 mm.

In a 6th aspect in accordance with any of the previous aspects, the proximal load bearing head (3) has an overall dimension in a plane orthogonal to the main axis (A) higher than 4 mm.

In a 7th aspect in accordance with any of the previous aspects, the insert is configured for treating the lesion of Hill-Sachs.

In an 8th aspect in accordance with any of the previous aspects, the insert is made of bio-compatible material, such as titanium alloy, polymer, medical steel or bone substitute, in particular the insert is made of a porous bio-compatible material, such as a bone substitute material including natural mineral matrix (e.g. of bovine origin), reinforced with biodegradable synthetic polymers and natural collagen (e.g. derivatives of bovine origin).

In a 9th aspect in accordance with any of the previous aspects, the proximal load bearing head (3) includes a blind or a through hollow (5), in particular the hollow (5) being centered on the main axis (A).

In a 10th aspect in accordance the previous aspect, the hollow (5) has a circular cross section and is in particular cylindrical in shape.

In an 11th aspect in accordance the previous aspect 9, the hollow (5) has a polygonal cross section.

In a 12th aspect in accordance with any of the previous three aspects, the blind hollow (5) has an extension along the main axis comprised between 2 mm and 10 mm, or the through hollow has a second opening (5b) in correspondence of the bottom surface (3c).

In a 13th aspect in accordance with any of the previous four aspects, the hollow (5) has an overall extension orthogonal to the main axis in the range between 1.5 mm and 4 mm.

In a 14th aspect in accordance with any of the previous aspects, the proximal load bearing head (3) has a slightly convex upper surface (3a), said surface being in particular smooth.

In a 15th aspect in accordance with any of the previous aspects, the proximal load bearing head (3) has a spherical upper surface (3a).

In a 16th aspect in accordance with any of the previous aspects, the proximal load bearing head (3) has a substantially spherical shape, in particular a radius of curvature being included in the range 17-30 mm.

In a 17th aspect in accordance with any of the previous aspects, the proximal load bearing head (3) comprises a lateral surface (3b), the upper surface (3a) is connected to the lateral surface (3b) by means of connecting regions having a radius of curvature of substantially 0.2-5 mm.

In an 18th aspect in accordance with any of the previous aspects, the proximal load bearing head (3) is equivalent or larger than the distal fixation body (2).

In a 19th aspect in accordance with any of the previous aspects, the proximal load bearing head (3) includes a lateral surface (3b) emerging from and extending transversal to the upper surface (3a), the lateral surface including a proximal portion (6) defining a surface parallel to the main axis (A) and a distal portion (7), extending from the proximal portion, defining a surface tapered in the direction of the main axis (A) moving towards the distal fixation body (2).

In a 20th aspect in accordance with any of the previous aspects, the proximal portion (6) is cylindrical.

In a 21st aspect in accordance with any of the previous two aspects, the proximal portion (6) of the lateral surface (3b) has an overall extension along the main axis (A) included between 3 mm and 10 mm.

In a 22nd aspect in accordance with any of the previous three aspects, an overall dimension of the distal portion (7) of the lateral surface (3b) in a plane orthogonal to the main axis (A) reduces, in particular progressively, moving towards the bottom surface (3c) or the distal fixation body (2), the distal portion (7) being for example convex.

In a 23rd aspect in accordance with any of the previous four aspects, the distal portion (7) is in the shape of a truncated cone.

In a 24th aspect in accordance with any of the previous five aspects, the distal portion (7) has an overall extension along the main axis (A) included between 1.5 mm and 4.5 mm.

In a 25th aspect in accordance with any of the previous six aspects, the proximal load bearing head (3) has an overall extension along the main axis (A) included between 5 mm and 12 mm.

In a 26th aspect in accordance with any of the previous seven aspects, the distal portion (7) plus the proximal portion (6) have an overall extension along the main axis (A) included between 5 mm and 12 mm.

In a 27th aspect in accordance with any of the previous eight aspects, a ratio (s/h) between the overall horizontal dimension (s) and the overall vertical dimension (h) of the proximal load bearing head (3) is comprised between 0.75 and 3, the ratio is in particular higher than (or equal to) 1.

In a 28th aspect in accordance with any of the previous nine aspects, a height ($h_1$) of the distal portion (7) is comprised between 25% and 75% of the overall vertical height (h), in particular the height ($h_1$) of the distal portion (7) being less than 50% of the overall vertical height (h) of the head (3).

In a 29th aspect in accordance with any of the previous ten aspects, a tapering angle (α) of the distal portion (7) is included between 5° and 30°, in particular between 7° and 25° and is optionally about 15°.

In a 30th aspect in accordance the previous aspect, a tapering angle (α) of the distal portion (7) included between 20° and 30° is associated with a height ($h_1$) of the distal portion (7) comprised between 50% and 75% of the overall vertical height (h) of the head (3).

In a 31st aspect in accordance the previous two aspects, a tapering angle (α) of the distal portion (7) included between 5° and 20° is associated with a height ($h_1$) of the distal portion (7) comprised between 25% and 50% of the overall vertical height (h) of the head (3).

In a 32nd aspect in accordance with any of the previous aspects, an overall dimension of the bottom surface (3c) is comprised between 22 mm and 3 mm.

In a 33rd aspect in accordance with any of the previous aspects, a difference between the maximum overall dimension (s) of the head (3) and the bottom surface (3c) in a plane orthogonal to the main axis (A) is less than 10 mm, in particular less than 5 mm.

In a 34th aspect in accordance with any of the previous aspects, the proximal load bearing head (3) includes a terminal junction surface (8) connecting the distal portion (7) of the lateral surface (3b) to the distal fixation body (2), the terminal junction surface (8) connecting the minimum overall extension of the distal portion (7) with the distal fixation body (2).

In a 35th aspect in accordance the previous aspect, the terminal junction surface (8) is configured to prevent sinking of the load bearing head (3) into the bone.

In a 36th aspect in accordance with any of the previous two aspects, the terminal junction surface (8) has an average inclination with respect to the main axis (A) of at least 45° and particularly of at least 60°.

In a 37th aspect in accordance with any of the previous two aspects, the terminal junction surface (8) is substantially a flat surface having an inclination with respect to the main axis (A) of at least 60° and particularly of about 90°.

In a 38th aspect in accordance with any of the previous two aspects, the terminal junction surface (8) is joined to the distal fixation body (2) by a contoured surface (11), such as a corner radius or a bevel.

In a 39th aspect in accordance the previous aspect, the contoured surface (11) is a corner radius of 0.2 to 5 mm, a preferred radius range being comprised between 2.5 and 3.5 mm.

In a 40th aspect in accordance with any of the previous aspects, the shaped lateral surface (2b) of the distal fixation body (2) comprises a plurality of ribbings (9) defining said undercuts (4), in particular said ribbings extending annularly around the distal fixation body (2).

In a 41st aspect in accordance with any of the previous aspects, the shaped lateral surface (2b) of the distal fixation body (2) comprises a plurality of parallel ribbings (9) defining said undercuts (4), in particular said ribbings extending annularly around the distal fixation body (2).

In a 42nd aspect in accordance with any of the previous aspects, the shaped lateral surface (2b) of the distal fixation body (2) comprises a plurality of ribbings (9) defining said undercuts (4), the ribbings having a profile in a longitudinal section and moving away from the proximal load bearing head (3) including:
  a first segment (9a) substantially orthogonal to, and moving away from, the main axis (A),
  a second segment (9b) emerging from the first segment and being substantially parallel to the main axis (A), and
  a third segment (9c) emerging from the second segment and transversal to the main axis (A), the third segment (9c) defining a progressive ribbing section reduction on moving along the main axis (A).

In a 43rd aspect in accordance the previous aspect, the third segment (9c) has a slope included in the range between 10° and 60°.

In a 44th aspect in accordance with any of the previous aspects, the distal fixation body (2) comprises a plurality of ribbings (9) in a number between 4 and 16.

In a 45th aspect in accordance with any of the previous aspects, the distal fixation body (2) comprises a distal end (10) having smooth surface with no shaped lateral surface (2b).

In a 46th aspect in accordance the previous aspect, a length of the distal end (10) along the main axis is comprised between 3 mm and 15 mm.

In a 47th aspect in accordance with any of the previous two aspects, the distal end (10) is in the shape of a truncated cone, in particular with rounded terminal portion in the form of a substantially spherical surface.

In a 48th aspect in accordance with any of the previous aspects, the distal fixation body (2) has an overall substantially cylindrical shape or an overall shape substantially in the form of a truncated cone.

In a 49th aspect in accordance with any of the previous aspects, the proximal load bearing head (3) has an overall dimension orthogonal to the main axis (A) which is at least 50% larger than an overall dimension orthogonal to the main axis (A) of the distal fixation body (2).

In a 50th aspect in accordance with any of the previous aspects, the proximal load bearing head (3) is larger than the distal fixation body (2), the proximal load bearing head (3) exhibiting a flat surface (8) substantially lying in a plane orthogonal to the main axis and joining a lateral surface (3b) of the proximal load bearing head (3) with the distal fixation body (2).

In a 51st aspect in accordance with any of the previous aspects, the distal fixation body (2) includes a thread defining said undercuts.

In a 52nd aspect in accordance the previous aspect, an angle formed by the helical surfaces of the thread is included between 45° and 90°.

In a 53rd aspect in accordance with any of the previous aspects, the distal fixation body (2) includes a thread with 4 to 16 threads.

In a 54th aspect in accordance with any of the previous three aspects, the distal fixation body (2) comprises a distal end (10) having the shape of a truncated cone with cone angles between 15° and 45°.

In a 55th independent aspect a use of an insert according to anyone of the previous aspects is provided for partial humeral joint reconstitution.

In a 56th independent aspect a use of an insert according to anyone of the previous aspects is provided for treating the Hill-Sachs lesion with partial humeral joint reconstitution.

In a 57th independent aspect a medical kit (100) for partial humeral joint reconstitution, in particular for treating the Hill-Sachs lesion provided, comprising: an insert according to anyone of the previous insert aspects; a cannulated body (101) having a handle (105) and a rigid cannula (102) with a longitudinal through hole axially extending for the whole instrument length from an insertion inlet (103) to an operating outlet (104); optionally a trocar (106) configured to be inserted into the hole of the cannulated body (101) and having, on one end, a knob (107) larger than the hole of the cannulated body and, on the other end, a tapered tip (108) configured to emerge from the operating outlet (104) when the trocar is coupled to the cannulated body (101); at least one osteochondral reamer (109) configured to be inserted into the cannulated body (101) and having, on a first end, a knob (110) larger than the hole of the cannulated body and, on a second end, a terminal punch (111) in the shape of a, preferably cylindrical, element with a sharp tip (111a), the reamer (109) also presenting a cutter (112) positioned at said second end immediately upstream the punch (111), the reamer (109) further including a torque transmitting portion (113), particularly at the first end, configured for coupling to a driving device for putting the cutter (112) into rotation, said torque transmitting portion being for example an AO Large coupling or similar attachment; a positioner (113) configured to be inserted into the cannulated body (101) and having, on a first end, a knob (120) larger than the hole of the cannulated body and, on a second end, a retaining portion (114), said retaining portion being configured to retain the insert, preferably by coupling of a pin (126) of the retaining portion (114) into a blind hollow (5) of the insert, and to position the insert in correspondence of a lesion to be treated, the positioner (113) including, on the first end, a head (120) to be hit e.g. with a hammer, and on the second end, an impact portion (114) substantially counter-shaped to the proximal load bearing head upper surface (3a) of the insert (1).

In a 58th aspect in accordance the previous aspect, the medical kit further includes an impactor (123) configured to be inserted into the cannulated body (101) and having, on a first end, a head (124) to be hit e.g. with a hammer, and on a second end, an impact portion (125) substantially counter-shaped to the proximal load bearing head upper surface (3a) of the insert (1).

In a 59th aspect in accordance with any of the previous two aspects, the rigid cannula (102) includes at least a lateral window (118) at the operating outlet (104) to allow for visual inspection, in particular the handle (105) having a visual indication (118) in direct alignment with said lateral window (118).

In a 60th aspect in accordance with any of the previous three aspects, the kit further including a comparator (119) configured to be inserted into the cannulated body (101) and having, on a first end, a knob (121) larger than the hollow of the cannulated body and, on a second end, a comparing portion (122) having a plurality of steps to allow checking extension of a humeral lesion.

In a 61st independent aspect a medical kit (100) for partial humeral joint reconstitution, in particular for treating the Hill-Sachs lesion provided, comprising:
an insert according to anyone of the previous insert aspects;
a surgical K-wire (201) having one end (201a) for fixing to a humeral joint lesion, the surgical K-wire (201) being in particular a Kirshner wire;
optionally at least one osteochondral reamer (209) configured to slide over the surgical K-wire (201) and presenting a cutter (212) positioned at a second end, the reamer (209) further including a torque transmitting portion (210), particularly at a first end, configured for coupling to a driving device for putting the cutter (212) into rotation, said torque transmitting portion being for example an AO Large coupling or similar attachment;
optionally a suture anchor fixation (202) with an anchor (203) to fix to the bone lesion and a suture (204), i.e. thread-like material used to sew tissue together, connected to the anchor (203).
a positioner (213), in particular configured to slide over the suture (204) or over the surgical K-wire (201), having, on a first end, a handle (220) and, on a second end, an active portion (214), said active portion being configured to position the insert in correspondence of a lesion to be treated, the positioner (213) including, on the first end, a head (220a) to be hit e.g. with a hammer, and on the second end, the active portion (214) substantially counter-shaped to the proximal load bearing head upper surface (3a) of the insert (1); and an impactor (223), in particular configured to slide over the suture (204) or over the surgical K-wire (201), having, on a first end, a head (224a) to be hit e.g. with a hammer, and on a second end, an impact portion (225) substantially counter-shaped to the proximal load bearing head upper surface (3a) of the insert (1).

In a 62nd aspect in accordance with the previous aspect, the surgical K-wire (201) is a sterilized, smooth metallic pin having a fixing element e.g. a thread, to fix the wire (201) at the lesion.

In a 63rd aspect in accordance with any of the previous two aspects, the kit further includes a comparator configured to slide over the surgical K-wire (201) and having, on a first end, a handle and, on a second end, a comparing portion having a plurality of steps to allow checking extension of a humeral lesion.

In a 64th aspect in accordance with any of the previous three aspects, the reamer (209) has a through passage (209a) with a development coincident with the main development axis of the reamer (209) and with an axis of rotation of the reamer itself, the through passage (209a) being sized to receive the surgical K-wire (201) so that the reamer is guided over the wire (201) during positioning and drilling operations, in particular, the through passage (209a) having a tapered opening (209b) in correspondence of a cutter tip.

In a 65th aspect in accordance with any of the previous four aspects, the reamer (209) further comprises a protector sleeve (208) externally covering the cutter (212) and at least one part of a reamer body to prevent damaging tissues during reamer insertion into the patient and prior drilling the seat into the bone, in particular the protector sleeve (208) being a cylindrical tube externally embracing the cutter (212).

In a 66th aspect in accordance with any of the previous five aspects, the reamer (209) further comprises an axial stop (211) provided in correspondence of a portion immediately upstream the cutter (212), the axial stop (211) defining a section enlargement of the reamer body with respect to the transversal section of the cutter (212) so as to prevent the cutter (212) to drill a too deep seat for the insert, the axial stop (211) defining an undercut (211a) configured to abut on the bone external surface.

In a 67th aspect in accordance with any of the previous six aspects, the positioner (213) has a through passage (213a) to allow the positioner (213) to slide over the suture (204) of the suture anchor fixation (202) or over the surgical K-wire (201), a section enlargement (213b) being provided in correspondence of the active portion (214) to allow an easier insertion over the suture (204) or surgical K-wire (201) and provide a coupling with a certain clearance.

In a 68th aspect in accordance with any of the previous seven aspects, the impactor (223) has a through passage (223a) to allow the impactor (223) to slide over the suture (204) of the suture anchor fixation (202) or over the surgical K-wire (201), the through passage (223a) presenting an enlargement in correspondence of the impact portion (225) to allow for an easier insertion over the suture (204) or surgical K-wire (201) and provide a coupling with a certain clearance, in particular the through passage (223a) having a back side lateral opening (223b) so that the impactor (223), when in use, may shift laterally towards an external contour of the upper head surface (3a) leaving a passage for the suture (204).

In a 69th aspect in accordance with any of the previous eight aspects, the impactor impact portion (225) has an asymmetrical shape, with a leg (226) emerging laterally from an impactor body, a length of the leg (226) being longer than half the overall horizontal span of the insert (1) to protrude over the upper head surface (3a).

In a 70th independent aspect a method for partial shoulder joint reconstitution is provided comprising the following steps: providing access to the humeral joint in correspondence of a lesion; defining a preliminary cavity in correspondence of the lesion of the humeral head, said cavity consisting in a proximal portion in the shape of a cylindrical or conical hollow with a substantially flat base, the proximal portion being defined by reaming the humeral bone; positioning a monolithic osteochondral local prosthetic insert (1) for partial humeral joint reconstitution, in particular of the type according to any of the insert aspects, in correspondence of said cavity; wherein the step of positioning includes the sub-step of inserting by press-fitting the insert into the cavity, the step of inserting causing a proximal load bearing head (3) defining an upper surface (3a) having a contour configured to substantially match the recipient's humeral head portion to house in the proximal portion of the cavity.

In a 71st aspect in accordance with the previous aspect, the step of providing access to the to the humeral joint in correspondence of the lesion includes fixing a surgical K-wire (201) substantially in the center of a humeral joint lesion, one end (201a) of the surgical K-wire (201) being fixed to the humeral lesion, the other end emerging from the humeral bone, the surgical K-wire (201) defining a path to accede to the lesion.

In a 72nd aspect in accordance with the previous aspect, the step of defining a preliminary cavity in correspondence of the lesion comprises inserting an osteochondral reamer (209) over the surgical K-wire (201) and sliding the osteochondral reamer (209) over the surgical K-wire (201) until a cutter (212) of the osteochondral reamer (209) reaches the lesion and putting the cutter (212) into rotation to define the cavity.

In a 73rd aspect in accordance with the previous aspect, the osteochondral reamer (209) includes an axial stop (211) fixed to a reamer body upstream the cutter (212) to prevent the cutter (212) to enter into the humeral bone more than a distance 'd' between the axial stop (211) and a cutter tip, the axial stop (211) abutting to a humeral bone external surface once the cavity has been completely drilled.

In a 74th aspect in accordance with any of the previous four aspects, the step of positioning a monolithic osteochondral local prosthetic insert (1) comprises positioning a suture anchor fixation (202) to the center of the cavity inside the lesion with an anchor (203) to fix to the bone lesion and a suture (204), i.e. thread-like material used to sew tissue together, connected to the anchor (203).

In a 75th aspect in accordance with the previous aspect, the step of positioning a monolithic osteochondral local prosthetic insert (1) comprises:
  inserting the monolithic osteochondral local prosthetic insert (1) over the suture (204) and sliding the monolithic osteochondral local prosthetic insert (1) over the suture (204) until reaching the lesion;
  inserting a positioner (213) over the suture (204) and sliding the positioner (213) over the suture (204) until an active portion (214) of the positioner (213) reaches the insert (1); and
  pushing the positioner (213) to press-fit the monolithic osteochondral local prosthetic insert (1) into the cavity.

In a 76th aspect in accordance with the previous aspect, the positioner (213) has, on a first end, a head (220a), and on a second end, the active portion (214) substantially counter-shaped to the proximal load bearing head upper surface (3a) of the insert (1); the step of pushing the positioner (213) to press-fit the monolithic osteochondral local prosthetic insert (1) into the cavity includes hitting e.g. with a hammer, the head (220a) of the positioner (213).

In a 77th aspect in accordance with any of the previous two aspects, the step of positioning a monolithic osteochondral local prosthetic insert (1) comprises, after the step of pushing with the positioner (213), further steps of:
  inserting an impactor (223) over the suture (204) and sliding the impactor (223) over the suture (204) until an impact portion (225) of the impactor (223) reaches the insert (1); and
  shaping the head upper surface (3a) of the insert (1) with the impact portion (225) of the impactor (223).

In a 78th aspect in accordance with the previous aspect, the step of shaping the head upper surface (3a) of the insert (1) includes conforming the head upper surface (3a) to create a continuity between the head upper surface (3a) of the insert and the external humeral bone surface around the insert.

In a 79th aspect in accordance with any of the previous two aspects, the step of shaping includes:
  positioning a leg (226) of the impact portion (225) emerging laterally from an impactor body over the insert, the leg (226) protruding externally of the upper head surface (3a) and contacting the humeral bone, too;
  hitting on the impactor (223) to shape the head upper surface (3a) of the insert with the leg (226);
  rotating the impactor (223) around its development axis to angularly displace the leg (226) in a different angular position over the insert;
  repeating the steps of hitting and rotating the impactor a plurality of times to shape the head upper surface (3a) of the insert (1) with the impact portion (225).

In an 80th aspect according to aspect 74, the method further comprises tying a tissue or a tendon in correspondence of the lesion with the suture (204).

In an 81st independent aspect a method for partial shoulder joint reconstitution is provided comprising the following steps: providing access to the humeral joint in correspondence of a lesion; defining a preliminary cavity in correspondence of the lesion of the humeral head, said cavity including a distal portion in the shape of a cylindrical or conical hollow and a proximal portion in the shape of a hollow of larger diameter, in particular, the distal portion being defined by hammering or pushing a corresponding tip into the humeral bone, said proximal portion being defined for example by reaming the humeral bone; positioning a monolithic osteochondral local prosthetic insert (1) for partial humeral joint reconstitution, in particular of the type according to any of the insert aspects, in correspondence of said cavity; wherein the step of positioning includes the sub-step of inserting, optionally press-fitting or screwing, the insert into the cavity, so that a distal fixation body (2) of the insert engages into the distal portion of the cavity, said distal portion of the cavity having a diameter less than a diameter of the distal fixation body, the step of inserting also causing a proximal load bearing head (3) defining an upper surface (3a) having a contour configured to substantially match the recipient's humeral head portion to house in the proximal portion of the cavity.

In an $82^{nd}$ aspect in accordance with any of the previous method aspects, the method is performed as arthroscopic or open surgery.

In an $83^{rd}$ aspect in accordance with any of the previous method aspects, the method is to treat the Hill-Sachs lesion.

In an $84^{th}$ aspect in accordance with any of the previous method aspects, the method is executed using the medical kit according to anyone of the medical kit claims.

In an $85^{th}$ aspect in accordance with any of the previous four aspects, the step of providing access to the humeral joint is achieved using an cannulated body (101) having a handle (105) and a rigid cannula (102) with a longitudinal through hole axially extending for the whole instrument length from an insertion inlet (103) to an operating outlet (104) and a trocar (106) configured to be inserted into the hole of the cannulated body (101) and having, on one end, a knob (107) larger than the hole of the cannulated body and, on the other end, a tapered tip (108) configured to emerge from the operating outlet (104) when the trocar is coupled to the cannulated body (101), the trocar (106) being inserted into the instrument (101) with emerging tapered tip (108) and instrument and trocar are inserted into the patient up to reaching a lesion to be treated.

In an $86^{th}$ aspect in accordance with any of the previous five aspects, the step of defining a preliminary cavity is achieved using an osteochondral reamer (109) configured to be inserted into a cannulated body (101) and having, on a first end, a knob (110) larger than a hole of the cannulated body and, on a second end, a terminal punch (111) in the shape of a, preferably cylindrical, element with a sharp tapered tip (111a), the reamer (109) also presenting a cutter (112) positioned at said second end immediately upstream the punch (111), the reamer (109) further including a torque transmitting portion (113), particularly at the first end, configured for coupling to a driving device for putting the cutter (112) into rotation, the reamer being hammered or pushed against the humeral bone so that the punch defines the distal portion of the preliminary cavity in the bone, the reamer being put into rotation so that the cutter defines the proximal portion of the preliminary cavity in the bone.

In an $87^{th}$ aspect in accordance with any of the previous six aspects, the step of press-fitting the insert into the cavity is achieved using a positioner (113) configured to be inserted into a cannulated body (101) and having, on a first end, a head (120) to be hit e.g. with a hammer, and on a second end, an impact portion (114) substantially counter-shaped to the proximal load bearing head upper surface (3a) of the insert (1), the press-fitting including the steps of hammering on the positioner (113) to cause the distal fixation body of the insert to enter and engage for the mechanical interference with the distal portion of the cavity and to cause the proximal load bearing head (3) of the insert to enter into the proximal portion of the cavity.

According to a further aspect, it is provided a monolithic local prosthetic insert, for insertion into a portion of a damaged articular surface, the insert having an articular proximal end and a distal bone fixation body. According to a further aspect, the local prosthetic insert has a shape in axial section that is cylindrical single-stage or multistage or truncated-cone or tapered or combined or asymmetric. According to a further aspect, the local prosthetic insert has a proximal end that has a larger diameter than the distal end. According to a further aspect, the local prosthetic insert has a proximal end with a convex surface to simulate the local bone sphericity or a flat one. According to a further aspect, the local prosthetic insert has a lateral surface that is, for a main part or along its entire length, geometrically profiled in such a manner as to prevent displacement. According to a further aspect, the local prosthetic insert has a proximal body with one or more recesses to allow the manipulation and the insertion of the insert in position in the bone lesion. According to a further aspect, the local prosthetic insert has an end with a tapered geometry. According to a further aspect, the local prosthetic insert is insertable in position by compression and/or by press-fit principle. According to a further aspect, the local prosthetic insert is made of biocompatible material. According to a further aspect, it is provided a monolithic local prosthetic insert for insertion into a portion of damaged articular surface with an articular proximal end and a threaded distal body. According to a further aspect, the local prosthetic insert has a shape, in axial section that is cylindrical single-stage, multistage, truncated-cone, tapered or combined. According to a further aspect, the local prosthetic insert has a proximal end larger in diameter than the distal end. According to a further aspect, the local prosthetic insert has a proximal end with a convex surface to simulate the local bone sphericity or flat. According to a further aspect, the local prosthetic insert has a lateral surface that is threaded, for a main part or along its entire length, in such a manner as to prevent displacement. According to a further aspect, the local prosthetic insert has a proximal body with one or more recesses to allow the manipulation and the screwing of the insert in position in the bone lesion through a dedicated instrument by transmission of a torque. According to a further aspect, the local prosthetic insert has an end with a tapered geometry. According to a further aspect, the local prosthetic insert is made of a monolithic rigid body of various shapes. According to a further aspect, the local prosthetic insert is cylindrical in shape with multi-stage or single-stage. According to a further aspect, the local prosthetic insert is conical in shape. According to a further aspect, the local prosthetic insert is truncated-cone in shape. According to a further aspect, the local prosthetic insert has a shape deriving from a combination of the cited different shapes. According to a further aspect, the local prosthetic insert has a proximal axial part exhibiting a greater diameter with respect to the distal portion part. According to a further aspect, the surface of the proximal end of the prosthetic insert is smooth to minimize friction and abrasion phenomena with the adjacent articular surfaces. According to a further aspect, the surface of the proximal end of the prosthetic insert is convex to conform to the sphericity of the humeral head. According to a further aspect, the proximal end has a smooth side surface along an axial depth greater than the thickness of bone cartilage. According to a further aspect, on the proximal surface of the insert there may be present one or more axial grooves preferably with a cylindrical or polygonal cross-section to allow the manipulation and implantation, through dedicated tools, of the prosthetic insert. According to a further aspect, the lateral surface of the prosthetic body in the distal portion has a variable axial length of a geometric shaping or coating such as to allow the maintenance of the engaging position and prevent the displacement of the insert. According to a further aspect, said geometry can be of non-return type or threaded. According to a further aspect, the end of the distal portion has a tapered shape to facilitate access in the spongy portion of the bone. According to a further aspect, the local humeral prosthetic insert can be made with biocompatible material. Non-limiting embodiments of the present invention will be described hereinafter.

BRIEF DESCRIPTION OF THE FIGURES

FIG. 12 shows a main perspective view of a prosthetic local insert with a threaded body;

FIG. 13 shows a side view of the insert of FIG. 12;

FIG. 14 shows a longitudinal axial section of the insert of FIG. 12;

FIG. 15 shows a detail view of the proximal portion of the insert of FIG. 12;

FIG. 16 shows a detail view of the distal portion of the insert of FIG. 12;

FIG. 17 shows a local perspective view of the proximal head of the insert of FIG. 12;

FIG. 18 shows a trocar part of a medical kit for the treatment of the Hill-Sachs lesion;

FIG. 19 shows a cannulated body part of a medical kit for the treatment of the Hill-Sachs lesion;

FIG. 20 shows the trocar of FIG. 18 and the cannulated body of FIG. 19 duly coupled;

FIG. 21 shows an osteochondral reamer part of a medical kit for the treatment of the Hill-Sachs lesion;

FIG. 22 shows the cannulated body of FIG. 19 in perspective view;

FIG. 23 shows the osteochondral reamer of FIG. 21 and the cannulated body of FIG. 19 duly coupled;

FIG. 24 shows a positioner part of a medical kit for the treatment of the Hill-Sachs lesion;

FIG. 24A is an enlarged portion of a distal end of the positioner of FIG. 24;

FIG. 25 shows the positioner of FIG. 24 and the cannulated body of FIG. 19 duly coupled;

FIG. 26 shows an impactor part of a medical kit for the treatment of the Hill-Sachs lesion;

FIG. 26A is an enlarged portion of a distal end of the impactor of FIG. 26;

FIG. 27 shows a comparator part of a medical kit for the treatment of the Hill-Sachs lesion;

FIG. 27A is an enlarged portion of a distal end of the comparator of FIG. 28;

FIG. 28 shows the comparator of FIG. 27 and the cannulated body of FIG. 19 duly coupled;

FIGS. 36 to 41 shows the steps of a method for treating Hill-Sacs lesions; and

DETAILED EMBODIMENT DESCRIPTION

A general description of preferred embodiments of the invention will be provided hereinafter with respect to the prosthetic insert, the medical kit for applying the insert and the method for shoulder joint reconstitution by treating the humeral head.

The Local Prosthetic Insert

Figure 7:
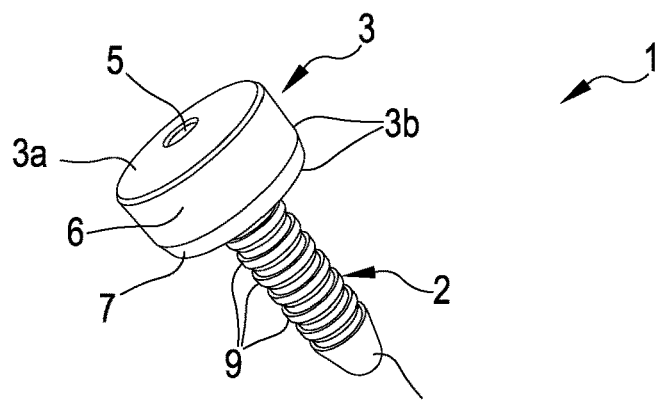
FIG. 7 shows a main perspective view of a prosthetic insert with dual-stage geometry.
Figure 8:
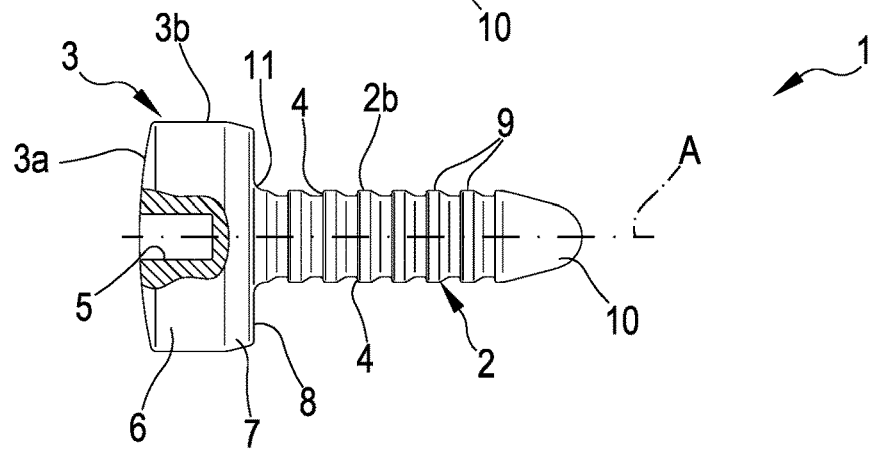
FIG. 8 shows a side view of the prosthetic insert of FIG. 7.
Figure 9:
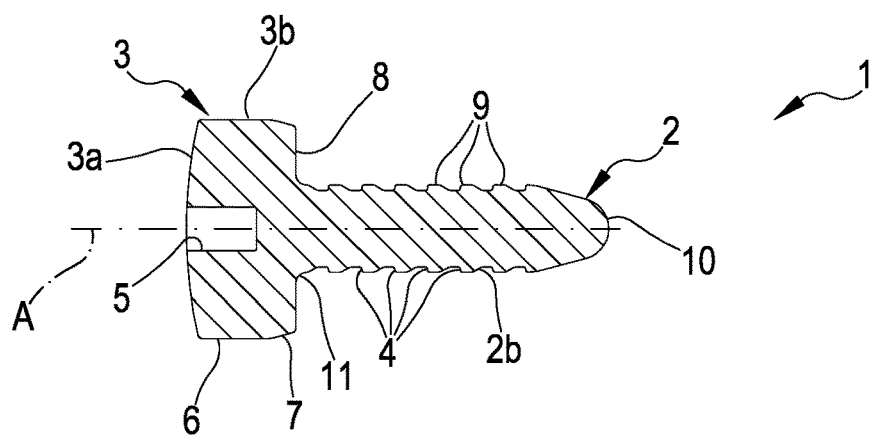
FIG. 9 shows a longitudinal axial section of the insert of FIG. 7.
Figure 10:
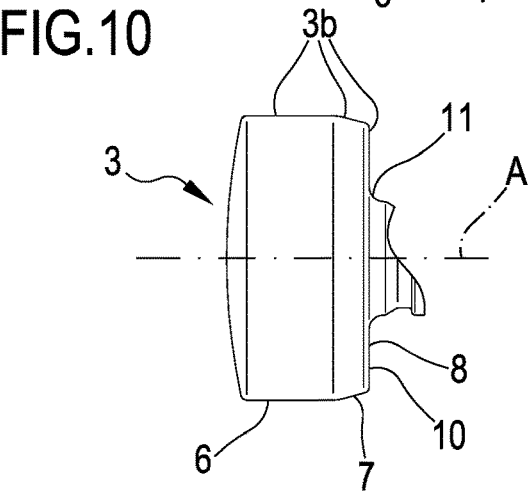
FIG. 10 shows a detail view of the proximal portion of the insert of FIG. 7.
Figure 11:
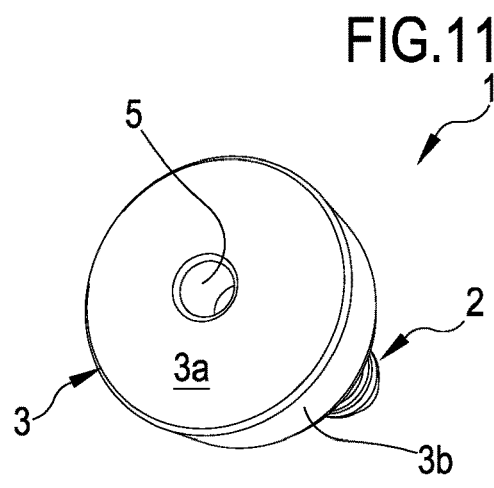
FIG. 11 shows a perspective view of the proximal head of the insert of FIG. 7.
Figure 30:
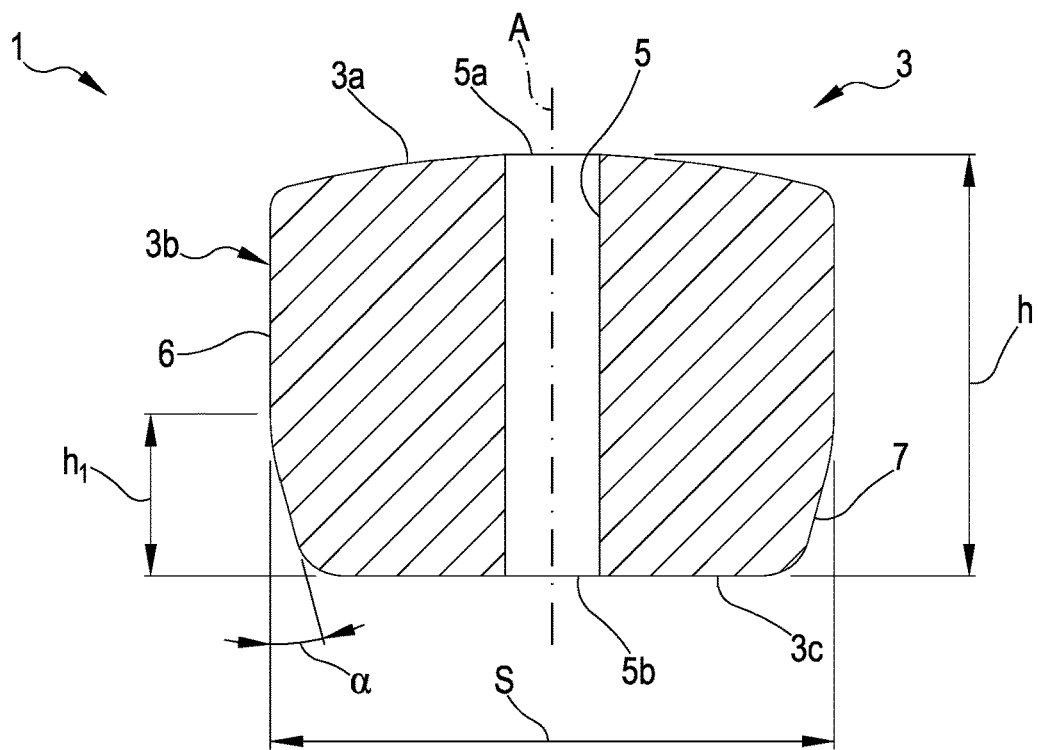
FIG. 30 shows a perspective view of a prosthetic local insert according to a further embodiment.
Figure 31:
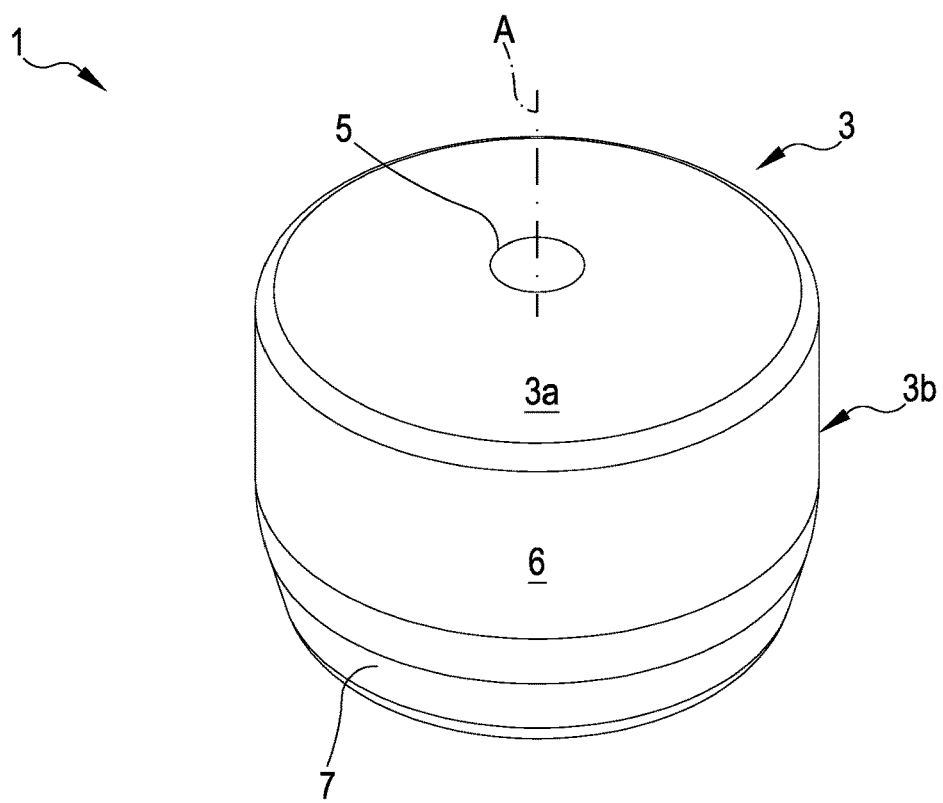
FIG. 31 shows a side view of the prosthetic insert of FIG. 30.
Figure 32:
FIG. 32 shows a surgical K-wire part of a kit according to an embodiment of the invention.

A monolithic osteochondral local prosthetic insert 1 for partial humeral joint reconstitution is disclosed in accordance with different embodiments. The first embodiments (FIG. 1-17) shows an insert 1 comprising a proximal load bearing head 3 defining an upper surface 3a having a contour destined to substantially or at least partially match the recipient's humeral joint portion and a distal fixation body 2 extending along a main axis A and configured for engaging the humeral bone head. The proximal load bearing head 3 and the distal fixation body 2 are monolithic and define a monolithic insert. An overall length of the insert 1 along the main axis A is comprised between 5 mm and 50 mm. In particular, the insert is configured for treating the lesion of Hill-Sachs. A further embodiment of a monolithic osteochondral local prosthetic insert 1 for partial humeral joint reconstitution is disclosed in FIGS. 30 and 31 and comprises a proximal load bearing head 3 defining an upper surface 3a having a contour destined to substantially or at least partially match the recipient's humeral joint portion only; no distal fixation body is provided in this different insert 1. Advantageously the insert is made of bio-compatible material, such as titanium alloy, polymer, medical steel or bone substitute. In embodiments according to FIGS. 1-17, the distal fixation body 2 comprises a shaped lateral surface 2b defining a plurality of undercuts 4 to substantially prevent distal fixation body extraction from the bone once the insert is properly positioned into the humeral head. Preferably the shaped lateral surface 2b of the distal fixation body 2 comprises a plurality of ribbings 9 defining the undercuts 4 (see e.g. FIGS. 1-11). In particular, though not essentially, the ribbings extend annularly around the distal fixation body 2. The ribbings shown in the annexed figures extend annularly and parallel one with the others around the distal fixation body 2. The geometric characteristics of this preferred embodiment make the prosthetic insert suitable for insertion in position into the bone by pressure, according to a "press-fit" principle. The shaping of the distal lateral surface is of non-return type, described for example as a "saw-tooth", whose function is to grip into the spongy portion of the bone. Along the distal lateral surface there are, preferably alternated according to a regular pattern, diametrical variations whose increase may be progressive, for example through a ramp having an inclination of approximately 10° to 60°. The surfaces are connected preferably via fillet radiuses. In more detail, looking at FIG. 5 (note that the ribbings of the embodiment of FIG. 7 are identical) the ribbings 9 exhibit a profile in a longitudinal section (moving away from the proximal load bearing head 3) including in sequence a first segment 9a substantially orthogonal to, and moving away from, the main axis A; a second segment 9b emerging from the first segment and being substantially parallel to the main axis A, and a third segment 9c emerging from the second segment and transversal to the main axis A. The third segment 9c defines a progressive ribbing section reduction on moving along the main axis A. Advantageously the third segment 9c has a slope included in the range between 10° and 60°. A fourth segment 9d, which is parallel to the main axis A (in case the distal fixation body is cylindrical) or slightly inclined (in case the distal fixation body 2 is a truncated cone), connects the third segment 9c, with the subsequent adjacent ribbing first segment 9a. Notably all segments 9a-9d are connected to the adjacent segments via reduced corner radius (e.g. 0.1-0.5 mm) to avoid sharp portions. Preferably the distal fixation body 2 comprises a plurality of ribbings 9 in a number between 4 and 16 placed along the axis at a distance between 1 and 3 mm, for example (e.g. pitch 1.5 mm). The distal fixation body 2 may comprise a distal end 10 having smooth surface with no shaped lateral surface 2b. A length of the distal end 10 along the main axis may be comprised between 3 mm and 15 mm (it is generally shorter than 5 mm). In the shown embodiments, the distal end 10 may be in the shape of a truncated cone, in particular with rounded terminal portion in the form of a substantially spherical surface (e.g. radius of about 1.4 mm). As previously mentioned, the distal fixation body 2 can have overall substantially cylindrical shape (FIGS. 1 and 7) or an overall shape substantially in the form of a truncated cone (FIG. 12). Advantageously the distal fixation body 2 has an overall dimension in a plane orthogonal to the main axis A included between 2 mm and 20 mm. In particular, in case the distal fixation body 2 is cylindrical, the diameter is less than 8 mm and preferably close to 4 mm. The distal fixation body 2 extends for at least 5 mm and is long less than 50 mm in the direction of the main axis A. Preferably an overall length of the distal fixation body 2 along the main axis A is comprised between 5 mm and 20 mm (e.g. less than 15 mm). The inserts 1 having ribbings 9 such as those shown in FIGS. 1-11 are adapted to be press-fitted into the humeral bone. A different embodiment is shown in FIGS. 12-17. In this technical solution, the distal fixation body 2 includes a thread defining the undercuts 4. An angle formed by the helical surfaces of the thread is included between 45° and 90° and the distal fixation body 2 may include a thread with 4 to 16 threads. Preferably the distal fixation body 2 comprises a distal end 10 with no threads and having the shape of a truncated cone with cone angles between 15° and 45°. Moving to the proximal load bearing head detailed description (unless specified the described technical features applies to all insert embodiments including the insert of FIGS. 30 and 31), the head 3 has an overall dimension in a plane orthogonal to the main axis A less than 25 mm. This maximum dimension is due to the fact that the insert is for reconstitution of the humeral head, particularly for treating Hill-Sachs lesion, and not for a complete humeral head resurfacing. The proximal load bearing head 3 has an overall dimension in a plane orthogonal to the main axis A higher than 4 mm. In general the proximal load bearing head 3 is larger than the distal fixation body 2 (if present). A kit of inserts may include a plurality of different inserts having the same distal fixation body geometry (if present) and dimensions and showing heads 3 with different diameter, e.g. 6, 8, 10, 12, 14 and 16 mm. An overall dimension between 6 and 16 would be suitable for treating most of the Hill-Sachs lesions. The proximal load bearing head 3 has a slightly convex upper surface 3a which is smooth. In the preferred embodiments, the proximal load bearing head 3 has a substantially spherical shape, in particular a radius of curvature being included in the range 17-30 mm that substantially matches the sphericity of most of the humeral heads (a suitable radius may be 23 mm). In the disclosed embodiments, the proximal load bearing head 3 includes a (e.g. blind) hollow 5, and in particular the hollow 5 is centered on the main axis A. Advantageously in the embodiments having the distal fixation body 2, the hollow 5 is a blind hollow; the blind hollow 5 of FIGS. 1-11 has a circular cross section and is in particular cylindrical in shape. Vice versa, the blind hollow 5 of FIGS. 12 to 17 shows a polygonal cross section. Indeed, the embodiment with threads needs to be screwed into the humeral bone and therefore a polygonal shape is necessitated in order to allow proper torque to be transmitted. Of course the hollow 5 of the embodiments of FIGS. 1-11 may be equivalently polygonal in shape or may have any other suitable shape. Preferably, the blind hollow 5 has an extension along the main axis comprised between 2 mm and 10 mm and an overall extension orthogonal to the main axis in the range between 1.5 mm and 4 mm. Differently, the embodiment of FIGS. 30 and 31, shows at least one through hollow 5 having a circular constant cross section. Of course the through hollow 5 may be equivalently polygonal in shape or may have any other suitable shape, either showing a constant or varying cross section. The trough hollow overall extension orthogonal to the main axis is in the range between 1.5 mm and 4 mm. In correspondence of the upper surface (and/or the lower surface), the through hollow 5 may include connecting radii. The proximal load bearing head 3 includes a lateral surface 3b emerging from and extending transversal to the upper surface 3a, The proximal load bearing head 3 can be connected to a lateral surface 3b by means of connecting regions having a radius of curvature of substantially 0.2-5 mm. The lateral surface includes a proximal portion 6 defining a surface parallel to the main axis A (i.e. a cylindrical portion) and a distal portion 7, extending from the proximal portion, defining a surface tapered in the direction of the main axis A moving towards the distal fixation body 2/towards the main axis A. Advantageously, the proximal portion 6 of the lateral surface 3b has an overall extension along the main axis A included between 0.1 mm and 5 mm. In particular, a connecting radius (e.g. radius=3 to 8 mm) connects adjacent proximal portion 6 and distal portion 7. Preferably, an overall dimension of the distal portion 7 of the lateral surface 3b in a plane orthogonal to the main axis A reduces, in particular progressively, moving towards the distal fixation body 2, the distal portion 7 being for example convex. The distal portion 7 can be in the shape of a truncated cone. The tapering angle may be less 30°, in particular less than 20° and about 15°. The progressive change of diameter along the transition surface between load bearing head and the distal fixation body allows the insert to be housed in position in the bone without causing the propagation of cracks in the bone cartilage surrounding the insertion point. Considering the embodiments of FIGS. 1-17, the lateral surface 3b includes a terminal junction surface 8 connecting the distal portion 7 to the distal fixation body 2. The terminal junction surface 8 connects the minimum overall extension of the distal portion 7 with the distal fixation body 2. The terminal junction surface 8 is configured to prevent sinking of the load bearing head 3 into the bone since the main forces acting on the insert are directed to push the insert towards and inside the humeral head. To this purpose, the terminal junction surface 8, which may assume any possible configuration, has however an average inclination with respect to the main axis A of at least 45° and particularly of at least 60°. The claimed angles are sufficient to exert a sufficient reaction normal to the pushing forces avoiding sinking. The embodiment of FIGS. 1-6 shows a terminal junction surface 8 that is slightly convex with an inclination much higher than 60° with respect to the main axis A. The embodiment of FIGS. 7-11 shows a terminal junction surface 8 that substantially a flat surface having an inclination with respect to the main axis (A) of about 90° (the proximal load bearing head 3 exhibits a flat surface substantially lying in a plane orthogonal to the main axis and joining a lateral surface 3b of the proximal load bearing head 3 with the distal fixation body 2). In case of the terminal junction surface 8 is defined by a flat orthogonal surface (see FIG. 8), the terminal junction itself is joined to the distal fixation body 2 by a contoured surface 11, such as a corner radius or a bevel. This contoured surface 11 allows distributing stresses, which may generate between the proximal load bearing head 3 and the distal fixation body 2 so that breaking of the monolithic insert is prevented. In case the contoured surface 11 is a corner radius a radius of 0.2 to 5 mm may be used depending on the differences in dimension between the head 3 and the body 2. A preferred range is comprised between 2.5 and 3.5 mm. The embodiment of FIGS. 12-17 shows a terminal junction surface 8 that is almost rectilinear with an inclination of about 60° with respect to the main axis A. The embodiment of FIGS. 30 and 31 differs from the other insert embodiments basically because no distal fixation body is provided. In this respect, the head 3 shows a bottom surface 3c which is planar or substantially planar. The distal portion 7 connects the proximal portion 6 to the bottom surface 3c (see FIG. 31). In particular, a connecting radius (e.g. radius=0.5 to 1.5 mm) connects adjacent distal portion 7 and bottom surface 3c. The overall vertical dimension h of the head 1 is comprised between 5 and 12 mm, and an absolute value would be about 6 mm. The ratio (s/h) between the overall horizontal dimension s and the overall vertical dimension h of the head 3 is comprised in the range between 0.75 and 3; in general however, the ratio is higher than (or equal to) 1, meaning that the head is larger than high. Furthermore, the height $h_1$ of the distal portion 7 is comprised between 25% and 75% of the overall vertical height h. For example, it may be included in the range 1.5-4.5 mm. The distal portion 7 reducing the overall horizontal dimension of the head cross section moving towards the bottom surface 3c has the aim to create an invitation for insert insertion into the lesion. In this respect the tapering angle should be less than 30° to avoid blocking against and/or crushing the bone. The highest is the angle, the lowest should be the distal portion overall height $h_1$. In this respect, an angle of about 30° would be associated with a distal portion height $h_1$ of about 25% the overall vertical height h of the head 3 (e.g. 1.5 mm). Vice versa, an angle of about 5° would be associated with a distal portion height $h_1$ of about 75% the overall vertical height h of the head 3 (e.g. 4.5 mm). Clearly, the bottom surface 3c should be larger enough to allow a proper resting on the bone surface. Therefore, the bottom surface should not be reduced too much. The bottom surface 3c overall dimension would be slightly lower that the head maximum overall dimension in a plane orthogonal to axis A, due to the tapering of the distal portion 7. The overall dimension of the bottom surface 3c is comprised between 22 mm and 3 mm. In particular, a difference between the maximum overall dimension of the head 3 and the bottom surface 3c in a plane orthogonal to axis A may be less than 10 mm, in particular less than 5 mm. The indicated sizes, angles, radiuses of curvature, and more generally the geometrical dimensions that characterize the local prosthetic insert can undergo changes with respect to those above described order to better adapt to the conditions and applications for which the local prosthetic insert is intended. Among the materials constituting the insert, bone substitute may be a valuable choice. The bone substitute may be produced by combining natural mineral bone structures (e.g. natural bovine bone mineral structures) with bioactive polymers and cell nutrients, allowing the patient's cells to grow quickly and efficiently into the bone substitute itself while its biopolymers degrade, providing perfect integration and osteogenesis. The bone substitute may be therefore composed of a natural mineral matrix of bovine origin, reinforced with biodegradable synthetic polymers and natural collagen derivatives of bovine origin. Macro- and microporous structure of the bone substitute should be similar to the structure of the human bone. The formation and growth of new bone in the implant site are promoted by the volume of the interconnected pores and by the natural composition. In time, the bone substitute is partly transformed by the osteoclasts and by the osteoblasts (physiological remodeling). Thanks to its properties, the bone substitute represents a valid alternative to the use of autologous bone: its high mechanical characteristics allow it to be cut to size with precision and facilitate implantation with specific osteosynthesis systems, also offering high grip. The combination of biopolymers and collagen derivatives facilitates blood retention and activates the cascade of regenerative signals in the defect site. Biopolymers and collagen derivatives are reabsorbed slowly over the course of several weeks while the substitute integrates with the receiving tissue. The manufacturing techniques for the realization of the local prosthetic insert, whether they are for chip removal or addition of material, melting, molding, mold or other, may influence the geometric characteristics described to allow the optimization of the production phase. The present invention also relates to the use of an insert as above described for partial humeral joint reconstitution. In particular, the invention relates to the use of such insert for treating the Hill-Sachs lesion with partial humeral joint reconstitution.

Medical Kit

The present invention also relates to a medical kit 100 for partial humeral joint reconstitution, in particular for treating the Hill-Sachs lesion, allowing the insert as above described to be used for partial humeral head reconstitution. There are currently different kits depending on the specific embodiment of the prosthetic insert. According to FIGS. 18 to 28, a first medical kit is described for partial humeral joint reconstitution using any of the inserts of FIGS. 1 to 17 and the process of FIG. 29. According to FIGS. 32 to 35, a second medical kit is described for partial humeral joint reconstitution using the insert according to FIGS. 30 and 31 and the process of FIG. 42.

First Medical Kit—FIGS. 18 to 28

Figure 29:
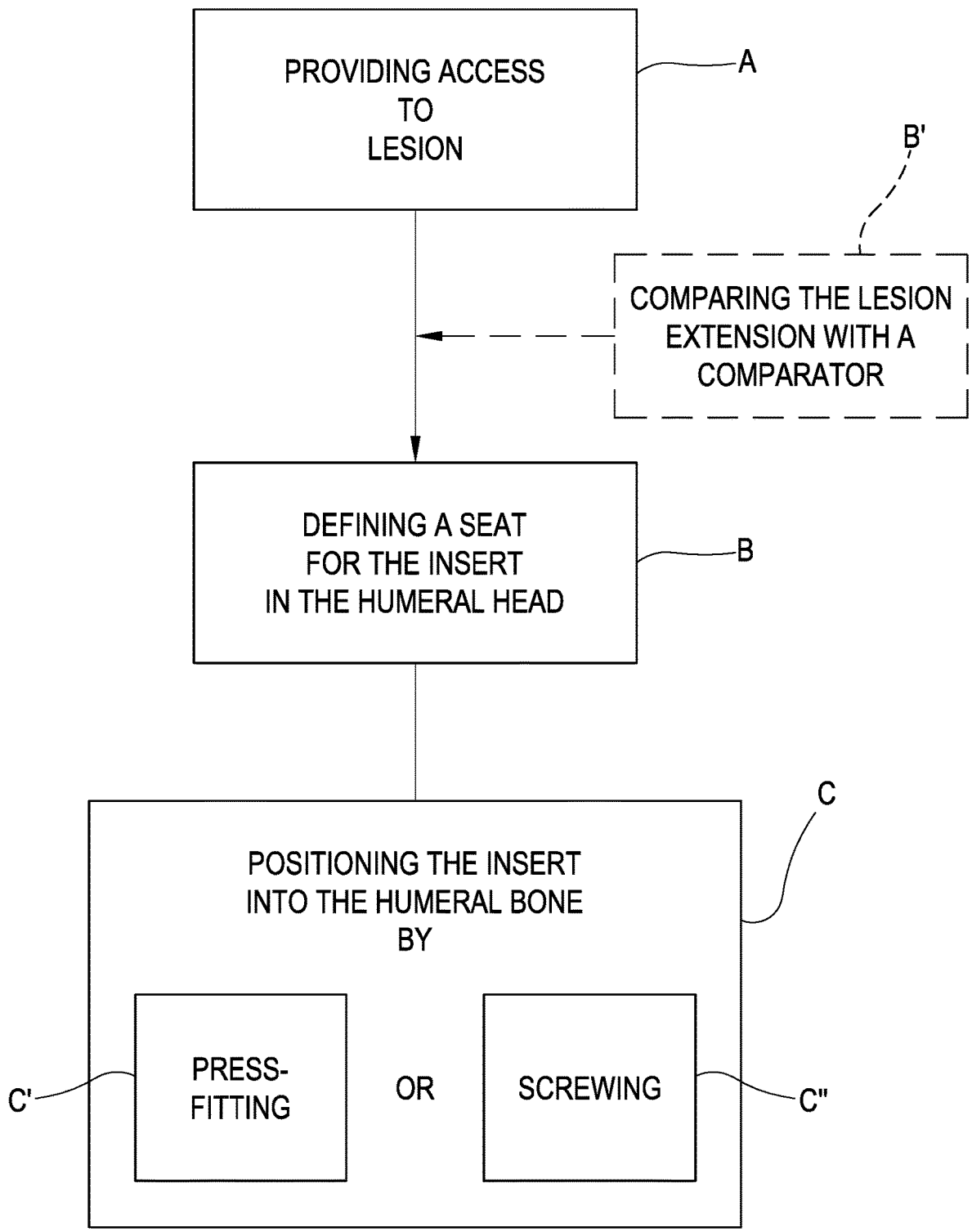
FIG. 29 shows a flow chart with the main surgical method steps.

The kit includes some medical instruments for implementing a three step surgical operation for the insert implant. The preferred embodiment is for arthroscopy since it is the less invasive surgical procedure; however, open surgery is equally applicable, substantially with the same or very similar medical kit. The medical kit comprises a cannulated body 101, shown in FIGS. 19 and 22, having a handle 105 and a rigid cannula 102 with a longitudinal through hole axially extending along the whole instrument length from an insertion inlet 103 to an operating outlet 104. The rigid cannula 102 may include at least a lateral window 118 at the operating outlet 104 to allow for visual inspection, particularly useful during arthroscopic procedures. It is noted that FIG. 19 shows a cannulated body with a plurality of small windows and a longer windows (where reference number 118 is placed). Any of these apertures may be used for visual inspection. However, the handle 105 may have a visual indication 118' in direct alignment with the longer lateral window 118 for helping the surgeon to locate a proper position for inspection, in case of need. The medical kit may also comprise a trocar 106, shown in FIG. 18, configured to be inserted into the hole of the cannulated body 101 and having, on one end, a knob 107 larger than the hole of the cannulated body and/or of the insertion inlet 103 and, on the other end, a tapered tip 108 configured to emerge from the operating outlet 104 when the trocar is coupled to the cannulated body 101, as shown in FIG. 20. The trocar 106 is coupled to the cannulated body in case of arthroscopic surgery so that the cannulated body may be more easily inserted into the scalpel cutting while the tapered tip of the trocar opens the tissues. The medical kit 100 may also comprise a comparator 119, shown in FIGS. 27 and 27a, configured to be inserted into the cannulated body 101 (as shown in FIG. 28) and having, on a first end, a knob 121 larger than the hole of the cannulated body and/or of the insertion inlet 103 and, on a second end, a comparing portion 122 (shown in detail in FIG. 27a) having a plurality of steps to allow check the extension of a humeral lesion. The comparator 119 may or may not be used depending on the cases. When the surgeon necessitates to more precisely estimate the lesion extension, he/she may insert the comparator prior using the reamer to visually determine the extension of the lesion by directly comparing the lesion with the step having the closer extension (and whose length is known). The medical kit 100 also comprises an osteochondral reamer 109, shown in FIG. 21, configured to be inserted into the cannulated body 101 (as shown in FIG. 23) and having, on a first end, a knob 110 larger than the hole of the cannulated body and/or of the insertion inlet 103 and, on a second end, a terminal punch 111 in the shape of a, preferably cylindrical, element with a sharp tip 111a; the reamer 109 also presents a cutter 112 positioned at the second end immediately upstream the punch 111. In coupled configuration, both the terminal punch 111 and the cutter 112 at least partly emerge from the outlet 104 of the cannulated body. The reamer 109 further includes a torque transmitting portion 113, particularly at the first end, configured for coupling to a driving device (not shown) for putting the cutter 112 into rotation. The torque transmitting portion 113 is configured to be attached to a proper electric medical apparatus to put the reamer into fast rotation allowing the cutter to properly remove humeral bone portions; the torque transmitting portion 113 may be an AO Large coupling or similar attachment. The medical kit 100 also comprises a positioner 113, shown in FIG. 24, configured to be inserted into the cannulated body 101 (as shown in FIG. 25) and having, on a first end, a knob 120 larger than the hole of the cannulated body and/or of the insertion inlet 103 and, on a second end, a retaining portion 114, the retaining portion 114 being configured to retain the insert, preferably by coupling a pin 126 of the retaining portion 114 into the blind hollow 5, and to allow to position the insert in correspondence of a lesion to be treated (see the detail of FIG. 24A). The retaining portion 114 has a slightly concave shape geometrically shaped to substantially match the shape of the slightly convex upper surface 3a of the proximal load bearing head 3 of the insert. In particular, the shape of the retaining portion is very similar to the enlarged particular of FIG. 26A apart the presence of the central pin, which enters the hollow 5 of the insert to withhold the insert itself. Furthermore, the positioner 113 has, on the first end, a head 120, adapted to be hit e.g. with a hammer; on the second end, the retaining portion 114, is substantially counter-shaped to the proximal load bearing head upper surface 3a of the insert 1 as mentioned so that the positioner allows to place the insert into the humeral bone. The medical kit 100 may also comprise an impactor 123 configured to be inserted into the cannulated body 101 and having, on a first end, a head 124 to be hit e.g. with a hammer, and on a second end, an impact portion 125 substantially counter-shaped to the proximal load bearing head upper surface 3a of the insert 1. The impactor 123 may be used subsequently to the use of the positioner 113 in case an additional position fine tuning is necessary; indeed, once the surgeon has inserted the prosthetic insert 1 with the positioner 113, the latter is removed and the operator checks the insert correct position. In some residual cases, it could be necessary to intervene on the insert to adjust the position. Though theoretically possible, it would be clearly difficult to use the positioner 113 again. Indeed, the presence of the central pin 126 to engage the hollow 5 of the insert 1 would require efforts to center the instrument, thereby at least increasing surgery time. Therefore, the impactor 123 may be used for the position modification since the latter does not have any pin emerging from the lower surface (see FIG. 26A) and may easily couple to the insert head. The present invention also relates to a three-step method for partial shoulder joint reconstitution comprising the following steps:

providing access to the humeral joint in correspondence of the lesion to be treated (see FIG. 29—reference A);

optionally using a comparator 119 in order for the surgeon to visually estimate the extension of the lesion to treat and decide the best insert to use (see FIG. 29—reference B');

defining a preliminary cavity in correspondence of the lesion of the humeral head, the cavity including a distal portion in the shape of a cylindrical or conical hollow and a proximal portion in the shape of a hollow of larger diameter, in particular, the distal portion being defined by pushing a corresponding tip into the humeral bone, the proximal portion being defined for example by reaming the humeral bone (see FIG. 29—reference B);

positioning a monolithic osteochondral local prosthetic insert 1 for partial humeral joint reconstitution, in particular of the type according to any of the insert claims, in correspondence of the cavity (see FIG. 29—reference C) wherein the positioning includes inserting (optionally press-fitting—FIG. 29, reference C' or screwing—FIG. 29, reference C") the insert 1 into the cavity, so that a distal fixation body 2 of the insert engages into the distal portion of the cavity, the distal portion of the cavity having a diameter less than a diameter of the distal fixation body, the step of inserting also causing a proximal load bearing head 3 defining an upper surface 3a having a contour destined to substantially match the recipient's humeral joint portion to house in the proximal portion of the cavity.

Figure 1:
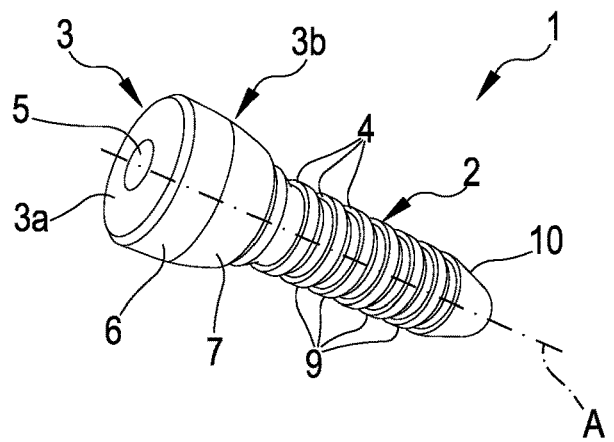
FIG. 1 shows a main perspective view of the shape of a prosthetic local insert with a non-return geometry.
Figure 2:
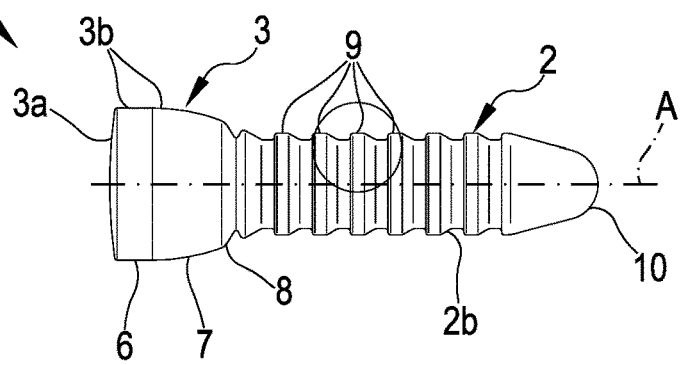
FIG. 2 shows a side view of the prosthetic insert of FIG. 1.
Figure 3:
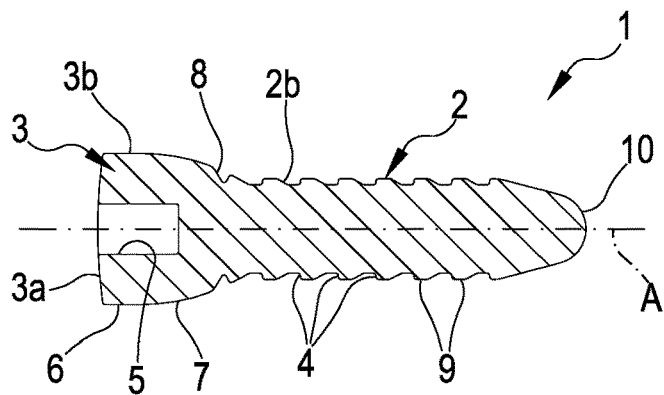
FIG. 3 shows a longitudinal axial section of the insert of FIG. 1.
Figure 4:
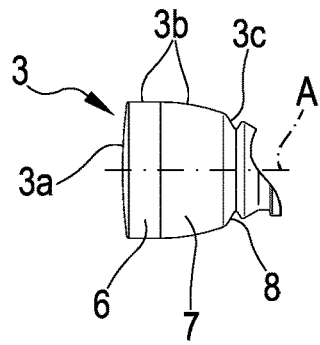
FIG. 4 shows a detail view of the proximal portion of the insert of FIG. 1.
Figure 5:
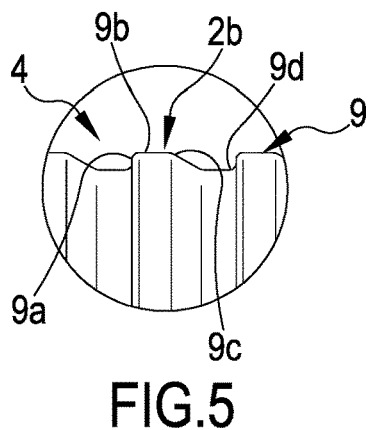
FIG. 5 shows an enlarged view of the lateral surface of the distal fixation body of the insert of FIG. 1.
Figure 6:
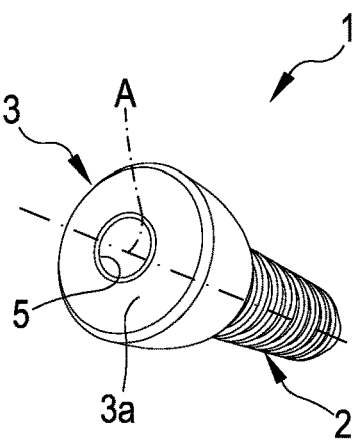
FIG. 6 shows a perspective view of the proximal head of the insert of FIG. 1.

As mentioned, the method may be preferentially executed in arthroscopy; however, it is not excluded the possibility to adopt open surgery. The step of providing access to the humeral joint may be achieved using the described cannulated body 101 with handle 105. The trocar 106 is inserted into the instrument 101 with emerging tapered tip 108 and instrument and trocar are inserted into the patient up to reaching a lesion to be treated. A surgeon or assistant keeps the cannulated body into position and a second surgeon or assistant proceeds with the operation. The step of defining a preliminary cavity may be achieved using the described osteochondral reamer 109 inserted into the cannulated body 101. The reamer is hammered (or pressed) against the humeral bone so that the punch defines the distal portion of the preliminary cavity in the bone; the reamer is also put into rotation so that the cutter removes humeral bone portions and defines the proximal portion of the preliminary cavity in the bone. Depending on the chosen insert, the positioning of the insert may include press-fitting (when inserts of FIG. 1 or 7 are used) or screwing in case the insert of FIG. 12 is used. In the first case, the step of press-fitting the insert into the cavity may be achieved using the positioner 113 once inserted into the cannulated body 101. The press-fitting includes the steps of hammering on the positioner head to cause the distal fixation body of the insert to enter and engage for the mechanical interference with the distal portion of the cavity and to cause the proximal load bearing head 3 of the insert to enter into the proximal portion of the cavity. Preferably, all the three-steps of method are executed in arthroscopy. In particular, the method is to treat the Hill-Sachs lesion. Preferably, but not exclusively, the method is executed using the medical kit as above described.

Second Medical Kit—FIGS. 32 to 35

Figure 33:
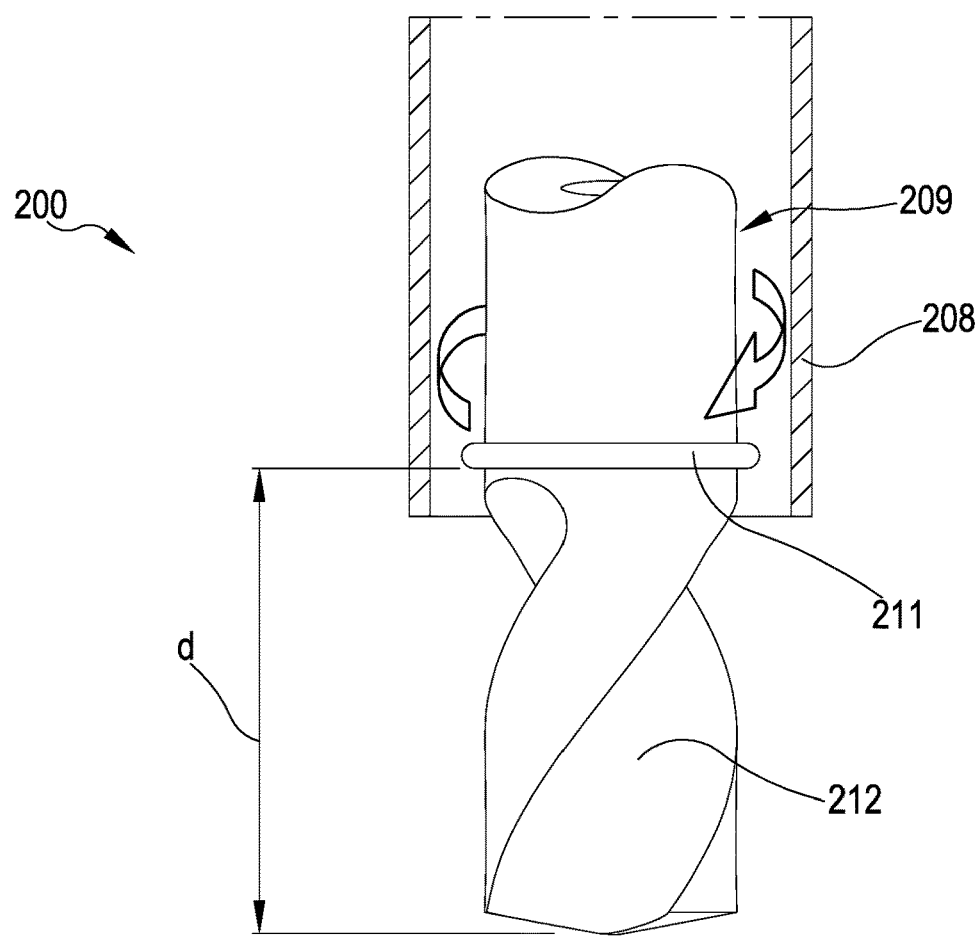
FIG. 33 shows a distal portion of a reamer part of a kit of an embodiment of the invention.
Figure 33A:
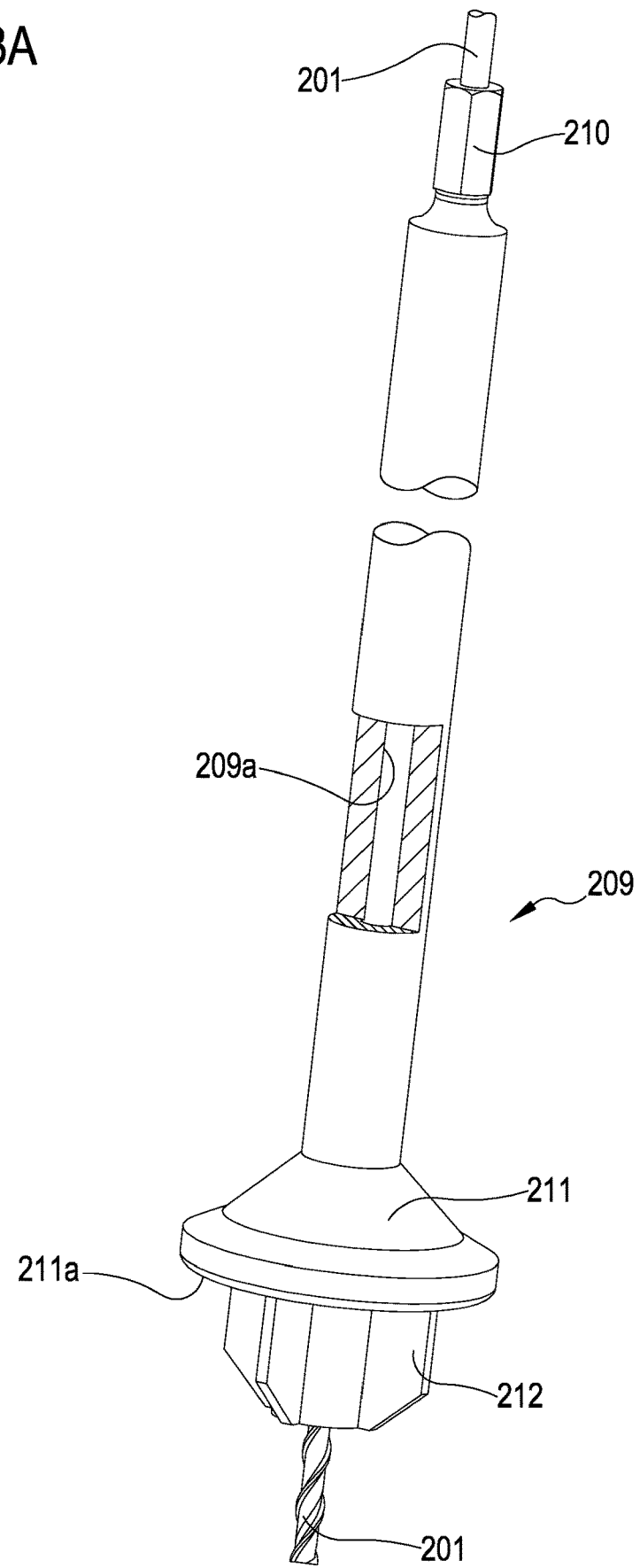
FIG. 33A shows an example of a reamer part of a kit of an embodiment of the invention.
Figure 33B:
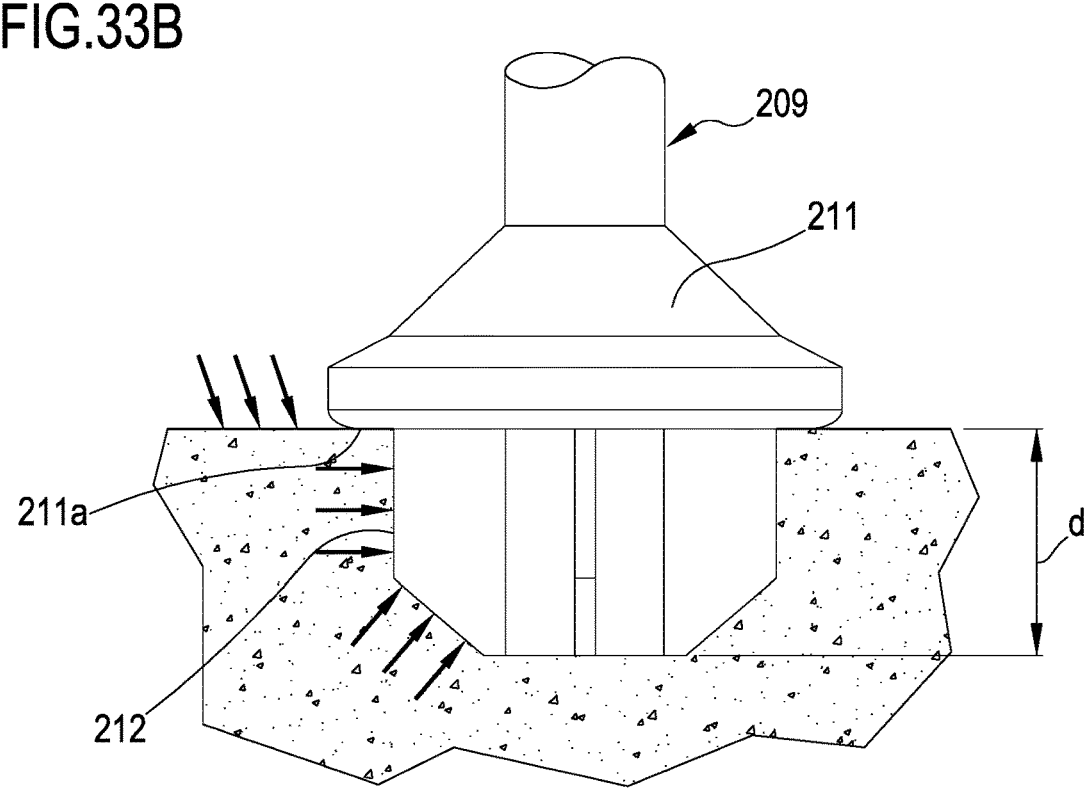
FIG. 33B shows the cutter of the reamer of FIG. 33A.
Figure 33C:
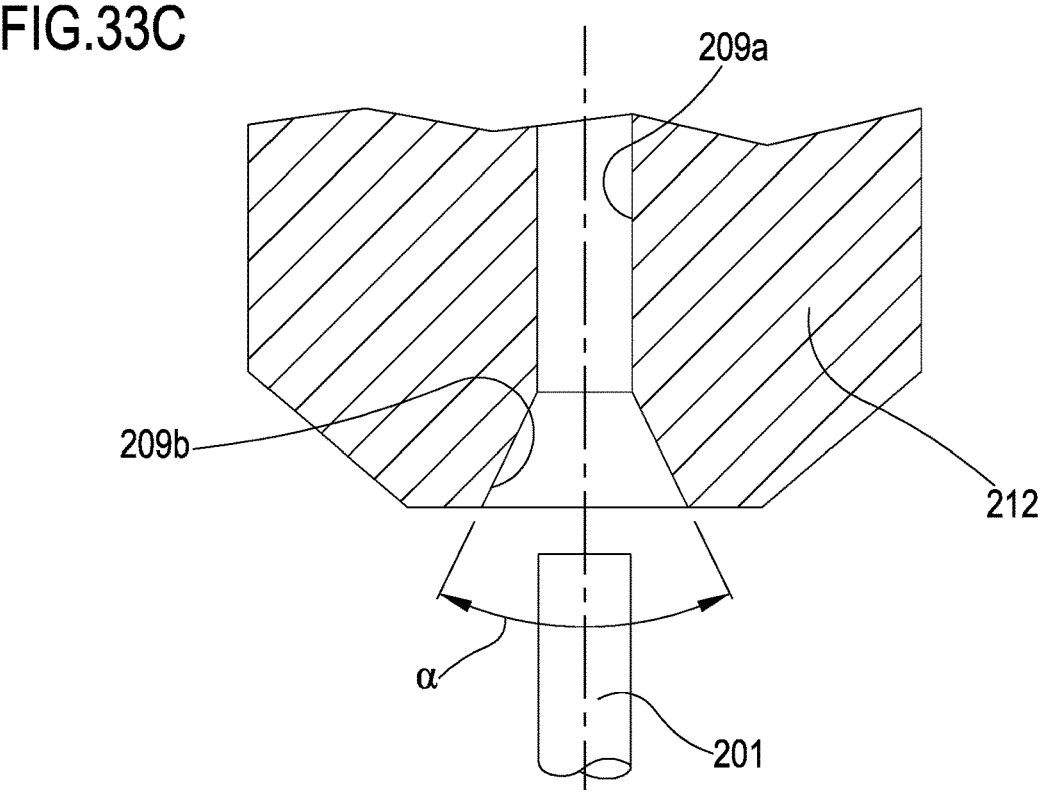
FIG. 33C is a partial section of the cutter of FIG. 33B.
Figure 33D:
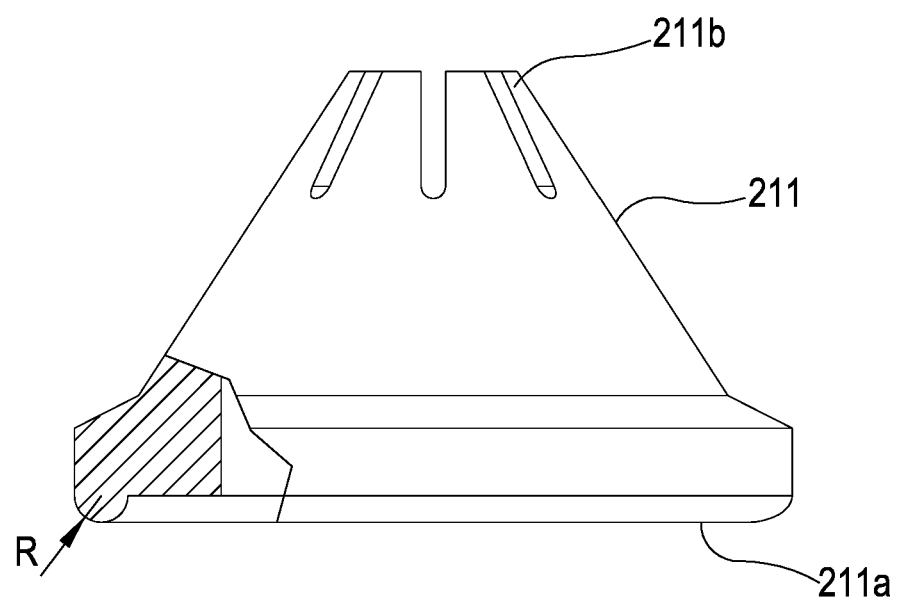
FIG. 33D is an axial stop embodiment to be fixed to a reamer.
Figure 33E:
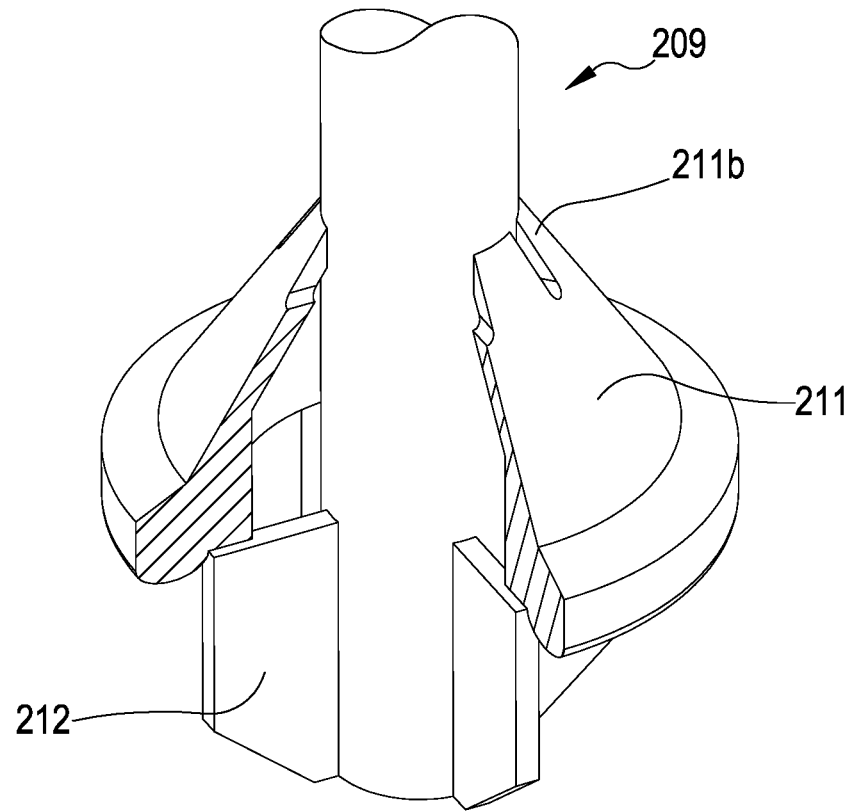
FIG. 33E is the axial stop of FIG. 33D fixed to a reamer portion.
Figure 42:
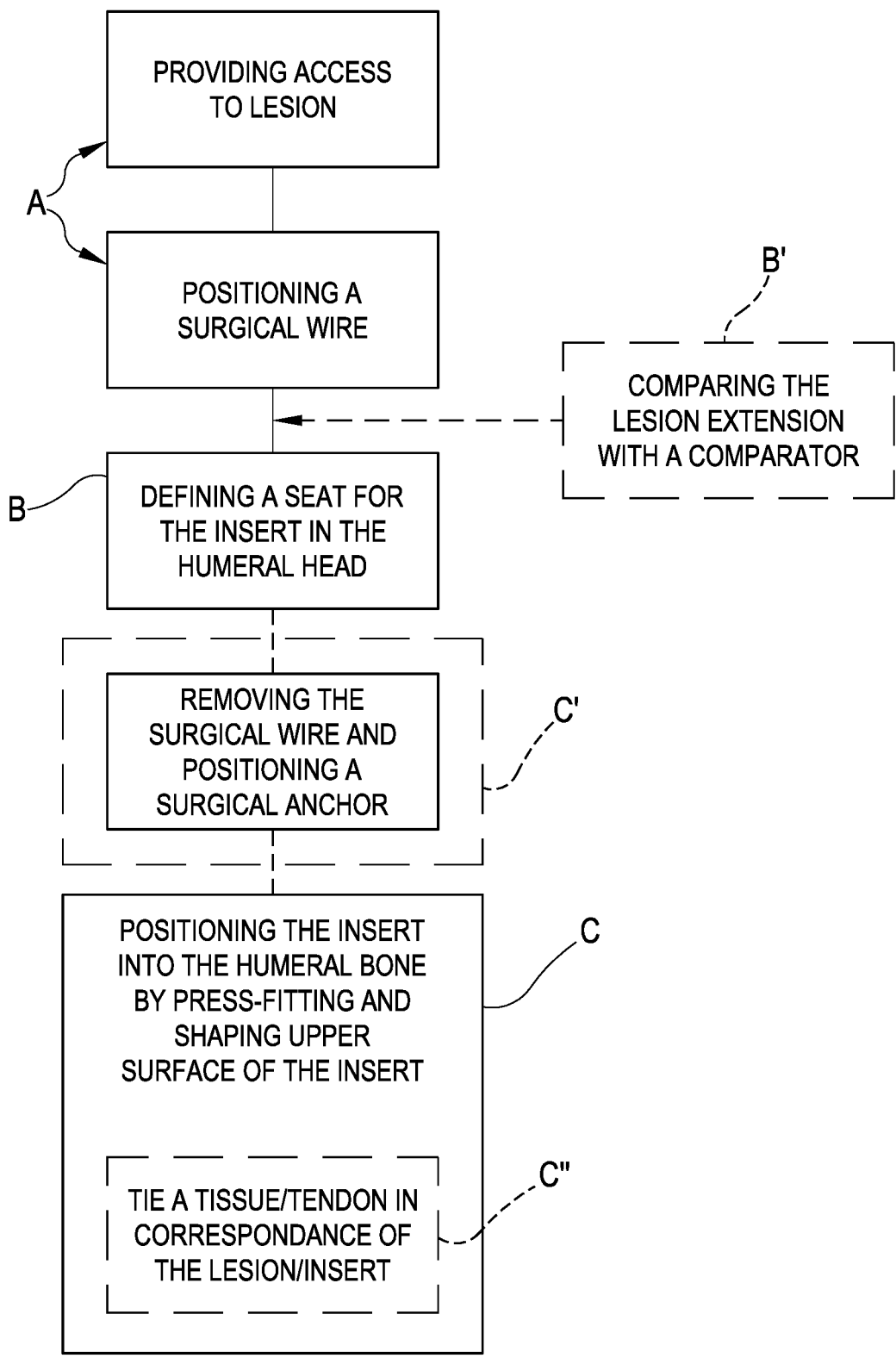
FIG. 42 shows a flow chart with the main surgical method steps of FIGS. 36 to 41.

The kit 200 includes some medical instruments for implementing a three step surgical operation for the insert implant. The preferred embodiment is for arthroscopy since it is the less invasive surgical procedure; however, open surgery is equally applicable, substantially with the same or very similar medical kit. The medical kit 200 comprises a surgical K-wire 201, i.e. a Kirschner wire or K-wire, which is a sterilized, sharpened, smooth stainless steel pin; see FIG. 32. The K-wire 201 is particularly threaded at least in correspondence of one end thereof 201a. For example, a K-wire having a length of about 250 mm and a diameter of 1.5 mm may be used. The surgical K-wire 201 is to be positioned centered into the humeral lesion as shown in FIG. 36. The medical kit 200 also comprises an osteochondral reamer 209, partially shown in FIG. 33, configured to slide over the K-wire (as shown in FIG. 37) and having, on a first end, a coupling 210 and, on a second end, a cutter 212. The cutter 212 is dimensioned so to create a seat in the humeral bone slightly smaller than the maximum overall horizontal dimension of the insert 1. In case the insert diameter (i.e. diameter of the proximal portion 6 of the insert 1) is e.g. 12 mm, the reamer 209 will be configured to drill a cavity in correspondence of the lesion having a diameter of e.g. 11 mm. The reamer 209 has a through passage 209a—see FIG. 33A—coincident with the main development axis of the reamer 209 (and with the axis of rotation of the reamer itself). The through passage 209a is sized to receive the surgical K-wire 201 so that the reamer is guided over the wire 201 during its positioning and during drilling operations. FIG. 33A shows the K-wire inserted into the reamer body from the cutter end to the other end. In particular, the through passage 209a may have a tapered opening 209b in correspondence of the cutter tip (see FIG. 33C). The tapering allows an easier insertion over the K-wire 201 and provides a coupling with a certain clearance to compensate for small shifting/tilting. The reamer 209 further includes a torque transmitting portion 210 (see FIG. 33A), particularly at the first end, configured for coupling to a driving device (not shown) for putting the cutter 212 into rotation. The torque transmitting portion 210 is configured to be attached to a proper electric medical apparatus to put the reamer into fast rotation allowing the cutter to properly remove humeral bone portions; the torque transmitting portion may be an AO Large coupling or similar attachment. The reamer 209, and in particular the cutter 212, may further comprise a protector sleeve 208 externally covering the cutter 212/the reamer body to prevent damaging tissues during reamer 209 insertion into the patient shoulder and prior drilling the seat into the bone. A protector sleeve 208 is shown in FIG. 33 only and basically consists of a tube externally embracing the reamer. Furthermore, an axial stop 211 is also provided in correspondence of a portion immediately upstream the cutter 212. The axial stop 211 defines an undercut 211a and has the aim to prevent the cutter 212 to drill a too deep seat for the insert. The axial stop 211 of FIG. 33 includes a ring or similar design configured to abut over the bone. Alternative designs are clearly available to the skilled person. For example, the axial stop 211 may be defined by a radial enlargement of the reamer body placed at a distance 'd' from the reamer tip equal to the maximum depth of the seat for the insert. FIG. 33B shows an embodiment of an axial stop 211 made in a single piece with the body of the reamer 209. As shown, the axial stop 211, being larger than the cutter 212 overall span, will lean over the bone surface and prevent any further drilling into the bone. Obviously, any suitable axial stop 211 may be used, such as a separate ring duly fixed at the reamer body at prefixed distance from the reamer tip, radially emerging pins or bumps, etc. FIG. 33D illustrates an axial stop 211 as a separate body connectable to the reamer body; FIG. 33E shows the axial stop of FIG. 33D removably attached to the reamer body. In particular an elastic portion 211b elastically deforms and slide over the reamer axial body until it reaches a seat (e.g. an annular groove) in the reamer body where it clamps and fix to the body. The medical kit 200 may also comprise a suture anchor fixation 202, e.g. an arthroscopic double-row suture anchor fixation (see FIG. 38). Suture anchor fixation 202 is a fixation device normally used for fixing tendons and ligaments to bone. It includes suture anchor fixation 202. The anchor 203 may use a screw mechanism or an interference fit (like a rawlbolt). It may be made of metal or biodegradable material (which dissolves in the body over time). The suture anchor fixation 202 further includes a suture 204, which is attached to the anchor 202 through an eyelet, which is a hole or a loop in the anchor 202 to through which the suture 204 passes. The suture 204 also may be a non-absorbable material or absorbable material. The medical kit 200 also comprises a positioner 213, shown in FIG. 34, configured to slide over the suture 204 of the suture anchor fixation 202 or over the surgical K-wire 201 (as only partially shown in FIG. 34A) and having, on a first end, a handle 220 and, on a second end, an active portion 214; the active portion 214 is configured for surface coupling to and for pushing the insert 1. In this respect, the active portion 214 has a slightly concave shape geometrically shaped to substantially match the shape of the slightly convex upper surface 3a of the proximal load bearing head 3 of the insert. In particular, the shape of the active portion mimics the radius of curvature of the upper surface 3a (being counter-shaped to a portion of such a surface 3a). Furthermore, the positioner 213 has, on the first end, a head 220a, adapted to be hit e.g. with a hammer; on the second end, the retaining portion 214, is substantially counter-shaped to the proximal load bearing head upper surface 3a of the insert 1 as mentioned so that the positioner allows to place the insert into the humeral bone. Also the positioner 213 has a through passage 213a to allow the positioner 213 to slide over the suture 204 of the suture anchor fixation 202 or over the surgical K-wire 201 (see FIG. 34A). A section enlargement 213b is provided in correspondence of the active portion 214 to allow an easier insertion over the suture 204 or K-wire 201 and provide a coupling with a certain clearance to compensate for small shifting/tilting. The medical kit 100 may also comprise an impactor 223 configured to slide over the suture 204 of the suture anchor fixation 202 or over the surgical K-wire 201 (as only partially shown in FIG. 35B) and having, on a first end, a handle 224 with a head 224a to be hit e.g. with a hammer, and on a second end, an impact portion 225 substantially counter-shaped to the proximal load bearing head upper surface 3a of the insert 1. The impactor 223 may be used subsequently to the use of the positioner 213 in case an additional position fine tuning is proper or necessary; indeed, once the surgeon has inserted the prosthetic insert 1 with the positioner 213, the latter is removed and the operator checks the insert correct position. Generally, it is proper to further intervene on the insert to shape the head surface 3a. Indeed, particularly when the insert is made of bone substitute, it is possible to use the impactor on the upper surface 3a in order to shaping the insert head contour to perfectly adapt to the lesion, i.e. so that there is no discontinuity between the insert upper surface and the bone surface. The impact portion 225 has an asymmetrical shape, with a leg 226 emerging from the impactor body. The length of the leg 226 is longer than half the overall horizontal span of the insert 1, so that, once the impactor 223 is in position (see FIG. 35B) a terminal portion of the leg 226 protrudes over the upper head surface 3a of the insert 1. Therefore, when the impactor 223 is hit on the head 224a, the impact portion acts to deform the upper head surface 3a in a way to conform to the humeral bone surrounding surface. The impactor 223 may be rotated so as to operate on the entire upper head surface 3a and to remove any discontinuity between the insert upper surface 3a and the humeral bone of the patient. Conveniently, the through passage 223a presents an enlargement in correspondence of the impact portion 225 to allow an easier insertion over the suture 204 or K-wire 201 and provide a coupling with a certain clearance to compensate for small shifting/tilting. Additionally, the through passage 223a may have a back side lateral opening 223b so that the impactor 223 can shift laterally towards the external contour of the upper head surface 3a leaving a passage for the suture 204; this is helpful when shaping the insert upper surface 3a. The present invention also relates to a three-step method for partial shoulder joint reconstitution comprising the following steps:

providing access to the humeral joint in correspondence of the lesion to be treated, included positioning a surgical K-wire (see FIG. 42—reference A);

optionally using a comparator 219 in order for the surgeon to visually estimate the extension of the lesion to treat and decide the best insert to use (see FIG. 42—reference B');

defining a preliminary cavity in correspondence of the lesion of the humeral head, the cavity exclusively including a proximal portion in the shape of a cylindrical hollow, the proximal portion being defined by reaming the humeral bone (see FIG. 42—reference B);

optionally removing the surgical K-wire and positioning a surgical anchor (see FIG. 42—reference C');

positioning a monolithic osteochondral local prosthetic insert 1 for partial humeral joint reconstitution, in particular of the type according to FIGS. 30 and 31, in correspondence of the cavity (see FIG. 42—reference C) wherein the positioning includes inserting, particularly by press-fitting the insert 1 into the cavity, so that a proximal head 3 of the insert engages into the proximal portion of the cavity by interference, the step of inserting also causing a proximal load bearing head 3 defining an upper surface 3a having a contour destined to substantially match the recipient's humeral joint portion to house in the proximal portion of the cavity; the positioning step further comprises a sub step of shaping the upper surface of the insert with the impactor and an optional final step of tying a tissue/tendon in correspondence of the lesion or the insert by means of the suture (see FIG. 42—reference C").

Figure 34:
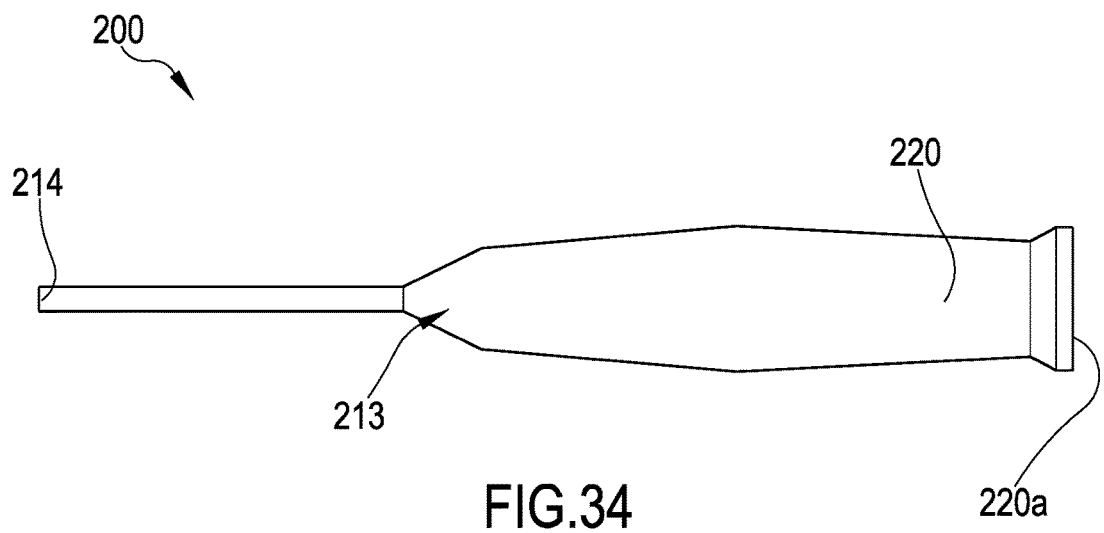
FIG. 34 shows a positioner of a kit according to an embodiment of the invention.
Figure 34A:
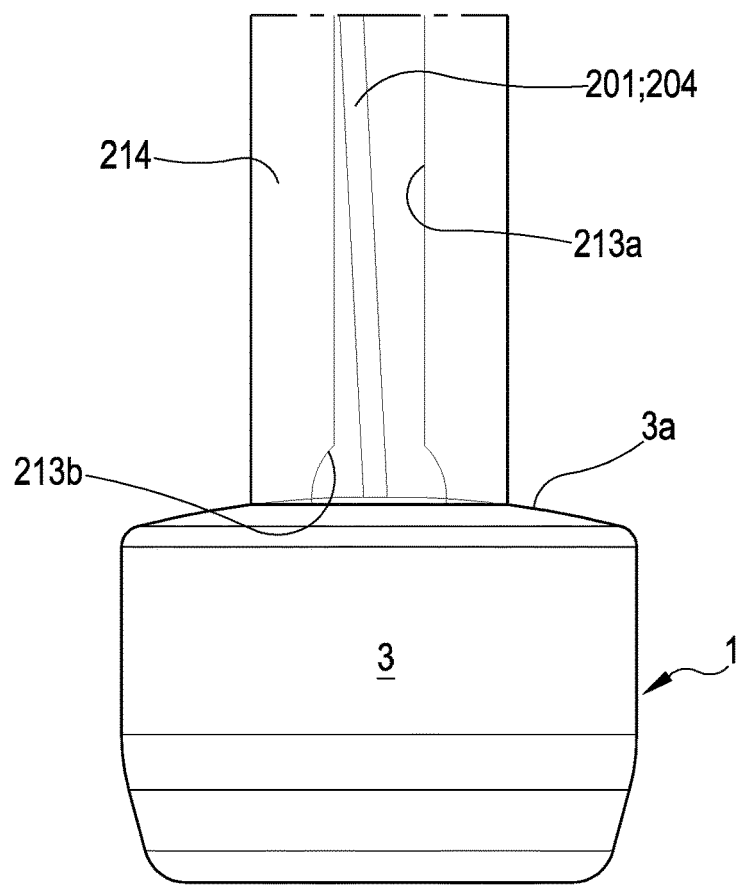
FIG. 34A shows an enlarged end of the positioner of FIG. 34 acting on the insert of FIG. 30.
Figure 35:
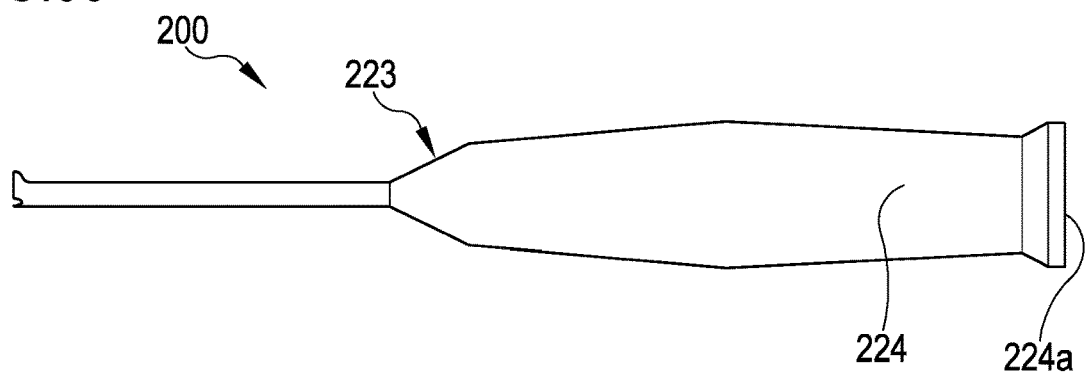
FIG. 35 shows an impactor of a kit according to an embodiment of the invention.
Figure 35A:
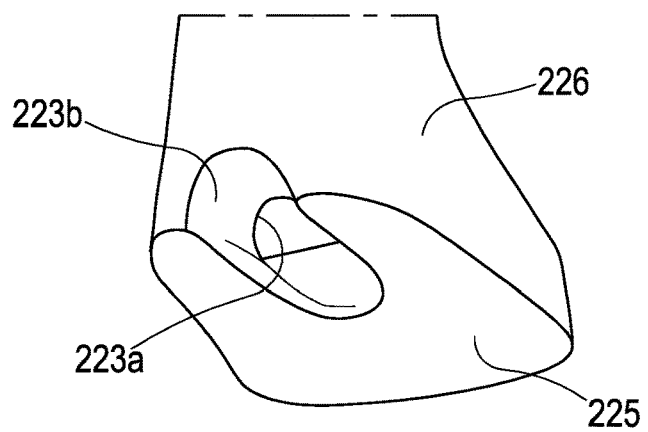
FIG. 35A shows an enlarged end of the impactor of FIG. 35.
Figure 35B:
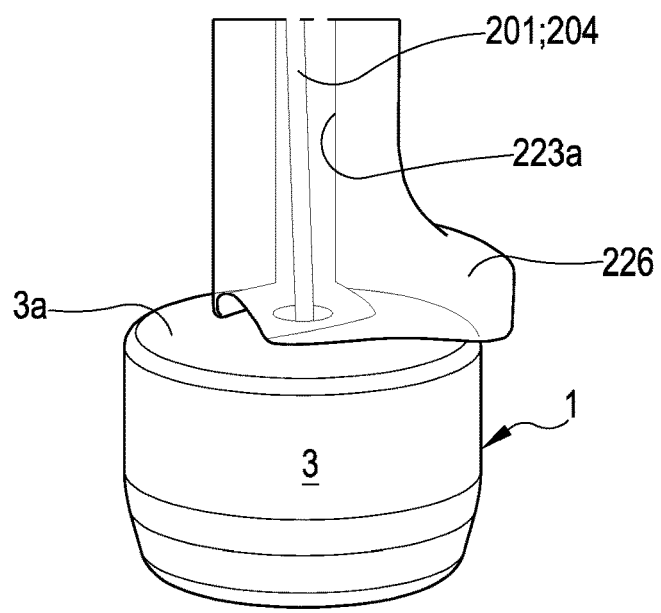
FIG. 35B shows the end of the impactor of FIG. 35A acting on the insert of FIG. 30.
Figure 39:
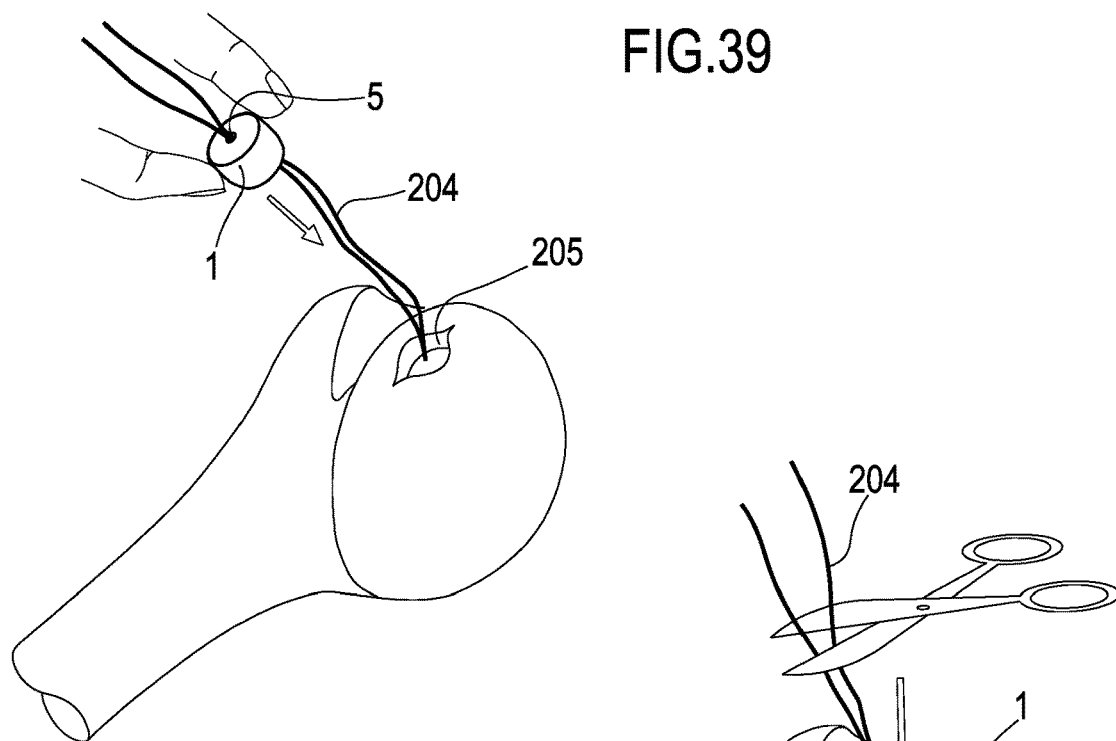
Figure 40:
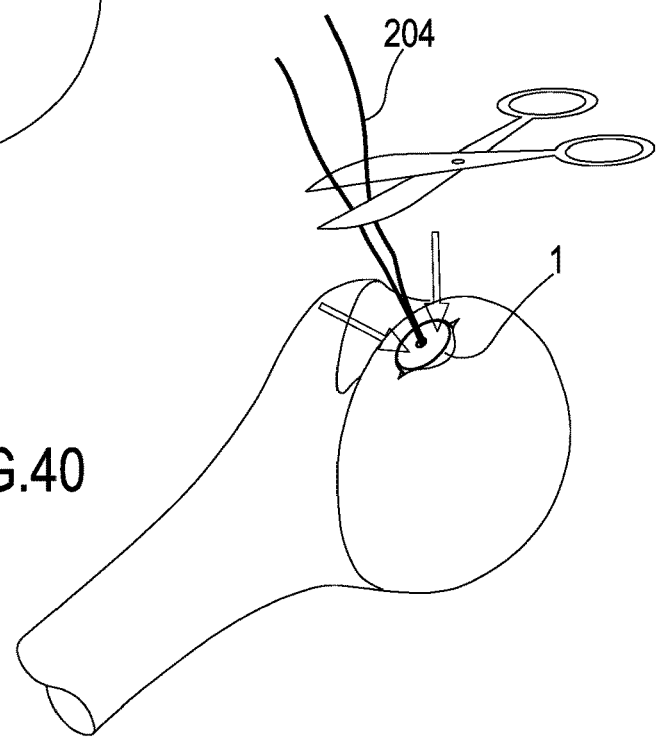
Figure 41:
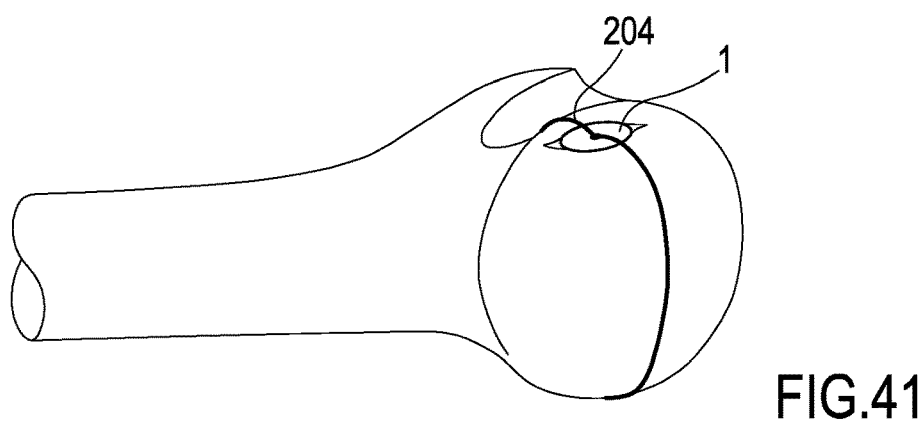

As mentioned, the method may be preferentially executed in arthroscopy; however, it is not excluded the possibility to adopt open surgery. The step of providing access to the humeral joint may be achieved with standard arthroscopy technique to position the K-wire 201 centered into the Hill-Sacs lesion. See exemplificative FIG. 36. The step of defining a preliminary cavity may be achieved using the described osteochondral reamer 209 inserted over the surgical K-wire 201. See exemplificative FIG. 37. The reamer is pressed against the humeral bone and is put into rotation so that the cutter 212 removes humeral bone portions and defines the proximal portion of the preliminary cavity in the bone. In particular, the K-wire 201 may be removed and the suture anchor fixing 202 coupled to the humeral bone in the center of the drilled seat 205. See exemplificative FIG. 38. Alternatively, though not preferred, the surgical K-wire 201 may be left into position and the step C performed with the K-wire 201 instead of the suture anchor fixation 202. The suture 204 is received into the through hollow 5 of the insert 1; in other terms, the anchor fixing 202 is used to guide the insert towards the right position into the drilled seat 205. See exemplificative FIG. 39. The drilled seat 205 has a slightly smaller diameter with respect to the diameter of the insert maximum overall span. Therefore, the positioning of the insert 1 includes press-fitting (when the insert of FIGS. 30 and 31 is used) into the drilled seat 205. The step of press-fitting the insert into the cavity may be achieved using the positioner 213. The positioner active surface 214 is placed over the upper head surface 3a as shown in FIG. 34A and the insert. The press-fitting includes the steps of hammering on the positioner head 220a to cause the proximal surface 6 of the head of the insert to enter and engage by mechanical interference with the cavity and to cause the proximal load bearing head 3 of the insert to position in an almost flush placement with respect to the remaining outer surface of the humeral bone. Then the impactor 223 is used. The anchor fixation 202 guides the impactor 223 via the through passage 223a so that the impact portion contact the upper surface 3a (as shown in FIG. 35B). The upper surface 3a is then shaped by e.g. hammering on the head 224a of the impactor 223 until all discontinuities between the insert and the bone upper surfaces are removed. Since insert 1 is preferably made of bone substitute, it will deform under the action of the impactor and precisely conform and adapt to the lesion cavity. In this situation (see FIG. 40) the suture 204 may be removed. Alternatively, the suture 204 may be used to tie a tendon portion or a tissue in correspondence of the lesion in case the surgeon considers it expedient or required to improve the lesion treatment. Preferably, all the three-steps of method are executed in arthroscopy. In particular, the method is to treat the Hill-Sachs lesion. Preferably, but not exclusively, the method is executed using any of the medical kits as above described.

Advantages

The present invention achieves various advantages. First of all, an osteochondral local prosthetic insert, a use of such insert, a method for partial humeral joint reconstitution and a medical kit for partial humeral joint reconstitution, according to the invention allow to overcome the drawbacks of the prior art techniques. Furthermore, the invention allows to obtain a local anatomical geometric reconstitution of a damaged articular surface allowing the local anatomical geometric reconstitution, in particular in case of Hill-Sachs lesions. Furthermore, the invention allows the joint stabilization in patients who have a Hill-Sachs lesion by reconstituting the geometric anatomical bone sphericity of the humeral head. Furthermore, the invention allows to restore the stability of the humeral head maintaining the full articular joint mobility and maintaining the patient's proprioception. Furthermore, the invention allows to treat the Hill-Sachs lesion without generating an additional load on the rotator cuff and/or joint capsule. The invention also allows to treat the Hill-Sachs lesion minimizing the invasiveness of the surgical intervention.

The invention claimed is:

1. A method for partial shoulder joint reconstitution comprising the following steps:
   providing access to a humeral joint in correspondence of a lesion of a humeral head;
   defining a cavity in correspondence of the lesion of the humeral head, said cavity consisting in a proximal portion in the shape of a cylindrical or conical hollow with a substantially flat base, the proximal portion being defined by reaming a humeral bone;
   positioning a monolithic osteochondral local prosthetic insert for partial humeral joint reconstitution in correspondence of said cavity, including:
   positioning a suture anchor fixation to a center of the cavity inside the lesion having an anchor to fix to the lesion and a suture connected to the anchor;
   inserting the monolithic osteochondral local prosthetic insert over the suture and sliding the monolithic osteochondral local prosthetic insert over the suture until reaching the lesion;
   inserting a positioner over the suture and sliding the positioner over the suture until an active portion of the positioner reaches the monolithic osteochondral local prosthetic insert;
   pushing the positioner to press-fit the monolithic osteochondral local prosthetic insert into the cavity;
   after the step of pushing the positioner, inserting an impactor over the suture and sliding the impactor over the suture until an impact portion of the impactor reaches the monolithic osteochondral local prosthetic insert and shaping a head upper surface of the monolithic osteochondral local prosthetic insert with the impact portion of the impactor;
   the step of inserting the impactor and shaping the head upper surface causing a proximal load bearing head to define the head upper surface having a contour configured to substantially match a recipient's humeral head portion, said proximal load bearing head being housed in the proximal portion of the cavity.

2. The method of claim 1, wherein the step of providing access to the humeral joint in correspondence of the lesion includes fixing a surgical K-wire substantially in the center of the cavity inside the lesion, one end of the surgical K-wire being fixed to the humeral lesion, the other end emerging from the humeral bone, the surgical K-wire defining a path to accede to the lesion.

3. The method of claim 2, wherein the step of defining the cavity in correspondence of the lesion comprises inserting an osteochondral reamer over the surgical K-wire and sliding the osteochondral reamer over the surgical K-wire until a cutter of the osteochondral reamer reaches the lesion and putting the cutter into rotation to define the cavity.

4. The method of claim 3, wherein the osteochondral reamer includes an axial stop fixed to a reamer body upstream the cutter to prevent the cutter from entering into the humeral bone more than a distance defined between the axial stop and a cutter tip, the axial stop abutting a humeral bone external surface once the cavity has been completely drilled.

5. The method of claim 1, wherein the positioner has, on a first end, a head, and on a second end, the active portion substantially counter-shaped to the head upper surface of the monolithic osteochondral local prosthetic insert; the step of pushing the positioner to press-fit the monolithic osteochondral local prosthetic insert into the cavity includes hitting the head of the positioner.

6. The method of claim 1, wherein the step of shaping the head upper surface of the monolithic osteochondral local prosthetic insert includes conforming the head upper surface of the monolithic osteochondral local prosthetic to create a continuity between the head upper surface of the monolithic osteochondral local prosthetic insert and an external humeral bone surface around the monolithic osteochondral local prosthetic insert.

7. The method of claim 1, wherein the step of shaping includes:
   positioning a leg of the impact portion emerging laterally from an impactor body over the monolithic osteochondral local prosthetic insert, the leg protruding externally of the head upper surface and contacting the humeral bone, too;

hitting on the impactor to shape the head upper surface of the monolithic osteochondral local prosthetic insert with the leg;

rotating the impactor around a development axis of the impactor to angularly displace the leg in a different angular position over the monolithic osteochondral local prosthetic insert;

repeating the steps of hitting and rotating the impactor a plurality of times to shape the head upper surface of the monolithic osteochondral local prosthetic insert with the impact portion.

8. The method of claim 1, further comprising tying a tissue or a tendon in correspondence of the lesion with the suture.

9. The method of claim 1, wherein the method is performed as arthroscopic or open surgery.

10. The method of claim 1, wherein the method is to treat a Hill-Sachs lesion.

11. A method for partial shoulder joint reconstitution is provided comprising the following steps:

providing access to a humeral joint in correspondence of a lesion of a humeral head;

defining a cavity in correspondence of the lesion of the humeral head, said cavity including a distal portion in the shape of a cylindrical or conical hollow and a proximal portion in the shape of a hollow of larger diameter, said proximal portion being defined by reaming a humeral bone;

positioning a monolithic osteochondral local prosthetic insert for partial humeral joint reconstitution in correspondence of said cavity;

wherein the step of positioning includes the sub-step of inserting the monolithic osteochondral local prosthetic insert into the cavity, so that a distal fixation body of the monolithic osteochondral local prosthetic insert engages into the distal portion of the cavity, said distal portion of the cavity having a diameter less than a diameter of the distal fixation body, the step of inserting also causing a proximal load bearing head defining an upper surface having a contour configured to substantially match a recipient's humeral head portion to house in the proximal portion of the cavity;

wherein the step of defining the cavity is achieved using an osteochondral reamer configured to be inserted into a cannulated body and having, on a first end, a knob larger than a hole of the cannulated body and, on a second end, a terminal punch in the shape of a cylindrical element with a sharp tapered tip, the osteochondral reamer also presenting a cutter positioned at said second end immediately upstream the terminal punch, the osteochondral reamer further including a torque transmitting portion, at the first end, configured for coupling to a driving device for putting the cutter into rotation, the osteochondral reamer being hammered or pushed against the humeral bone so that the terminal punch defines the distal portion of the cavity in the humeral bone, the osteochondral reamer being put into rotation so that the cutter defines the proximal portion of the cavity in the humeral bone.

12. The method of claim 11, wherein the step of providing access to the humeral joint is achieved using an cannulated body having a handle and a rigid cannula with a longitudinal through hole axially extending for a whole cannulated body length which is measured from an insertion inlet to an operating outlet and a trocar configured to be inserted into the hole of the cannulated body and having, on one end, a knob larger than the hole of the cannulated body and, on the other end, a tapered tip configured to emerge from the operating outlet when the trocar is coupled to the cannulated body, the trocar being inserted into the cannulated body with emerging tapered tip, wherein the cannulated body and the trocar are inserted into a patient up to reaching the lesion to be treated.

13. The method of claim 11, further comprising a sub-step of press-fitting the monolithic osteochondral local prosthetic insert into the cavity using a positioner configured to be inserted into the cannulated body and having, on a first end, a head to be hit, and on a second end, an impact portion substantially counter shaped to the proximal load bearing head upper surface of the monolithic osteochondral local prosthetic insert, the press-fitting including the steps of hammering on the positioner to cause the distal fixation body of the monolithic osteochondral local prosthetic insert to enter and engage for mechanical interference with the distal portion of the cavity and to cause the proximal load bearing head of the monolithic osteochondral local prosthetic insert to enter into the proximal portion of the cavity.

* * * * *